United States Patent
Chen et al.

(10) Patent No.: US 10,472,369 B2
(45) Date of Patent: Nov. 12, 2019

(54) CRYSTALLINE FORMS OF (6-(1H-INDAZOL-6-YL)-N-[4-(4-(4-MORPHOLINYL)PHENYL] IMIDAZO[1,2-A]PYRAZIN-8-AMINE) METHANESULFONATE

(71) Applicant: Crystal Pharmatech Co., Ltd., Suzhou, Jiangsu (CN)

(72) Inventors: Minhua Chen, Suzhou (CN); Yanfeng Zhang, Suzhou (CN); Po Zou, Suzhou (CN); Xiaoyu Zhang, Suzhou (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 16/079,764

(22) PCT Filed: Feb. 24, 2017

(86) PCT No.: PCT/CN2017/074729
§ 371 (c)(1),
(2) Date: Aug. 24, 2018

(87) PCT Pub. No.: WO2017/144010
PCT Pub. Date: Aug. 31, 2017

(65) Prior Publication Data
US 2019/0055255 A1    Feb. 21, 2019

(30) Foreign Application Priority Data

Feb. 26, 2016 (CN) .......................... 2016 1 0107825
Apr. 7, 2016 (CN) .......................... 2016 1 0214091

(51) Int. Cl.
*C07D 487/04* (2006.01)
*A61K 31/5377* (2006.01)

(52) U.S. Cl.
CPC ........ *C07D 487/04* (2013.01); *C07B 2200/13* (2013.01)

(58) Field of Classification Search
CPC ............ A61K 31/5377; C07B 2200/13; C07D 487/04
See application file for complete search history.

(56) References Cited

FOREIGN PATENT DOCUMENTS

| WO | 2015/017460 A1 | 2/2015 | |
|---|---|---|---|
| WO | WO 2015/017460 | * 2/2015 | ........... C07D 487/04 |

* cited by examiner

*Primary Examiner* — Erich A Leeser
(74) *Attorney, Agent, or Firm* — McCarter & English, LLP; Steven G. Davis; Wei Song

(57) ABSTRACT

The present disclosure relates to novel crystalline form I, form II and form III of 6-(1H-indazol-6-yl)-N-[4-(4-morpholinyl)phenyl]imidazo [1,2-a]pyrazin-8-amine mesylate, and preparation methods and use thereof. Crystalline form I is a dimesylate, and its X-ray powder diffraction pattern shows characteristic peaks at 2theta values of 5.9°±0.2°, 13.5°±0.2° and 21.8°±0.2°. Crystalline form II is a dimesylate, and its X-ray powder diffraction pattern shows characteristic peaks at 2theta values of 15.8°±±0.2°, 17.2°±0.2° and 19.5°±0.2°. Crystalline form III is a monomesylate, and its X-ray powder diffraction pattern shows characteristic peaks at 2theta values of 7.4°±0.2°, 12.9°±0.2° and 19.2°±0.2°. The crystalline forms are more suitable for drug development than prior crystalline forms, and the preparation methods for the crystalline forms are simple and repeatable and have significant value for future drug optimization and development.

29 Claims, 15 Drawing Sheets

CRYSTALLINE FORMS OF (6-(1H-INDAZOL-6-YL)-N-[4-(4-(4-MORPHOLINYL)PHENYL] IMIDAZO[1,2-A]PYRAZIN-8-AMINE) METHANESULFONATE

CROSS-REFERENCE TO RELATED APPLICATIONS

The present application is a U.S. national stage application, filed under 35 U.S.C. § 371(c), of International Application No. PCT/CN2017/074729, filed on Feb. 24, 2017, which claims the priority of Chinese Application No. 201610214091.8, filed on Apr. 7, 2016; and Chinese Application No. 201610107825.2, filed on Feb. 26, 2016. The entire contents of the aforementioned application are incorporated herein by reference.

TECHNICAL FIELD

The present disclosure relates to the field of pharmaceutical chemistry, particularly relates to crystalline forms of 6-(1H-indazol-6-yl)-N-[4-(4-morpholinyl) phenyl] imidazo [1, 2-a]pyrazin-8-amine monomesylate and dimesylate and preparation methods thereof.

BACKGROUND

Spleen tyrosine kinase was first cloned from porcine spleen cDNA at the earliest time by Japanese scholar Taniguchi, et al. Its coding protein is a non-receptor tyrosine kinase, so it is named as spleen tyrosine kinase. The spleen tyrosine kinase plays an important role in the maturation of lymphocytes and the activation of immune cells. In recent years, it is found that SYK has abnormal expression in tumor, and SYK has close relation with a lot of signals that relate to tumorincidence, progression andmigration. SYK may be used as a target for treating tumors related to immune systems, such as lymphoma, leukemia and the like.

Entospletinib is an orally administered drug developed by Gilead. It is a selective Spleen tyrosine kinase (SYK) inhibitor, which inhibits the activity of spleen tyrosine kinase, and has a therapeutic effect on various diseases including cancer and inflammation. Entospletinib is in clinical studies for the treatment of patients with relapsed or refractory chronic lymphocytic leukemia. The chemical name of the drug is 6-(1H-indazole-6-yl))-N-[4-(4-morpholinyl))phenyl]imidazo [1,2-a]pyrazine-8-amine, and the structure of compound (I) is shown as below:

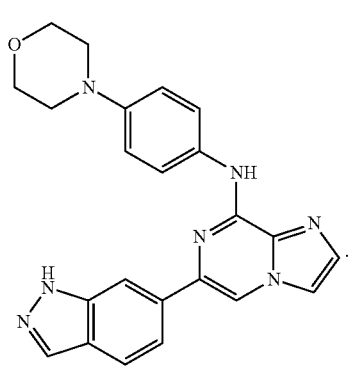

(I)

It is generally known that crystalline forms greatly affect drug's quality. Different crystalline forms may have remarkable difference in appearance, solubility, melting point, dissolution profile, bioavailability and so on, thus affect drug's stability, bioavailability and efficacy. Therefore, it is of great significance to develop novel and more suitable crystalline forms for drug development.

As is known to the skilled in the art, the presence of new solid polymorphs of a known chemical substance solid is unpredictable. The existence or the number of the polymorphs is also unpredictable. In addition, it is also unpredictable that under what conditions a specific form will crystallize, and what are the characteristics of the polymorphic form. Since different polymorphs have different properties (e.g., solubility, stability), their performances on drug's use and storage are different, it is necessary to study all solid forms, including all polymorphs to provide drugs with improved stability or solubility.

At present, only two hydrates of compound (I) dimesylate were reported in US20150038505A1, namely crystalline form 3 and crystalline form 7 (hereinafter referred to as prior form 3 and prior form 7). As reported in the prior art, the hygroscopicity of prior form 7 is very high under various humidity conditions. Relatively, prior form 3 is a more preferable crystalline form, because its hygroscopicity is relatively low under 70% humidity, and its solubility is significantly improved compared to the free base and amorphous monomesylate. However, the prior form 3 is found that it has 20% weight gain in high humidity conditions (above 80% humidity), and will convert to prior form 7 at 90% humidity, thus prior form 3 cannot meet the strict property requirements of crystal or drug product in industrial production and later drug development. Furthermore, although US20150038505A1 reported more than one method to obtain prior form 3, the methods are complicated and not easy to conduct. In addition, study on the particle size distribution showed that crystal grains size of prior form 3 and prior form 7 are too small to separate in production.

Accordingly, there is still a need to develop novel crystalline forms of compound (I) or its salts, which are more suitable to pharmaceutical formulations and can be obtained by more easily repeatable methods.

SUMMARY

One objective of the present disclosure is to provide novel crystalline forms of compound (I) mesylate, specifically to provide crystalline form I of compound (I) dimesylate, crystalline form II of compound (I) dimesylate, and crystalline form III of compound (I) monomesylate.

Another objective of the present disclosure is to provide preparation methods and uses of the above crystalline forms.

The compound (I) of the present disclosure is shown as follows:

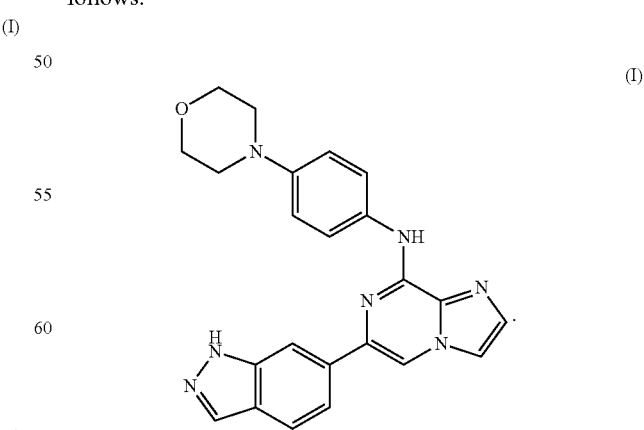

(I)

The X-ray powder diffraction pattern of crystalline form I of compound (I) dimesylate of the present disclosure (hereinafter referred to as form I of the present disclosure) shows characteristic peaks at 2theta values of 5.9°±0.2°, 13.5°±0.2° and 21.8°±0.2°.

Furthermore, the X-ray powder diffraction pattern of form I of the present disclosure preferably shows one or two or three characteristic peaks at 2theta values of 25.9°±0.2°, 17.1°±0.2° and 20.4°±0.2°.

More preferably, the X-ray powder diffraction pattern of form I of the present disclosure further shows one or two or three characteristic peaks at 2theta values of 10.6°±0.2°, 14.7°±0.2° and 17.7°±0.2°.

According to a specific and preferred aspect of the present disclosure, the X-ray powder diffraction pattern of form I of the present disclosure shows characteristic peaks at 2theta values of 5.9°±0.2°, 13.5°±0.2°, 21.8°±0.2°, 25.9°±0.2°, 17.1°±0.2°, 20.4°±0.2°, 10.6°±0.2°, 14.7°±0.2° and 17.7°±0.2°.

The present disclosure further provides a preparation method of form I of the present disclosure. The method comprises: a) adding compound (I) dimesylate into a mixed system of multiple organic solvents, and stirring at 5-30° C.; b) filtering the suspension of step a) and drying the filter cake to obtain form I of the present disclosure.

Furthermore, said mixed system of multiple organic solvents is preferably a mixed system of alcohol solvents and aromatic hydrocarbon solvents. In step a), more preferably, said stirring is at 20-30° C.

The X-ray powder diffraction pattern of crystalline form II of compound (I) dimesylate of the present disclosure (hereinafter referred to as form II of the present disclosure) shows characteristic peaks at 2theta values of 15.8°±0.2°, 17.2°±0.2° and 19.5°±0.2°.

The X-ray powder diffraction pattern of form II of the present disclosure shows one or two or three characteristic peaks at 2theta values of 26.1°±0.2°, 14.7°±0.2° and 21.9°±0.2°.

Furthermore, the X-ray powder diffraction pattern of form II of the present disclosure further shows one or two or three characteristic peaks at 2theta values of 7.6°±0.2°, 18.2°±0.2° and 27.8°±0.2°.

According to a specific and preferred aspect of the present disclosure, the X-ray powder diffraction pattern of form II of the present disclosure shows characteristic peaks at 2theta values of 15.8°±0.2°, 17.2°±0.2°, 19.5°±0.2°, 26.1°±0.2°, 14.7°±0.2°, 21.9°±0.2°, 7.6°±0.2°, 18.2°±0.2° and 27.8°±0.2°.

The present disclosure further provides a preparation method of form II of the present disclosure. The method comprises: a) adding compound (I) dimesylate into one or more aromatic hydrocarbon solvents, and stirring at 40-80° C.; b) filtering the suspension of step a) and drying the filter cake to obtain form II.

Preferably, in step a) of preparation method of form II, said aromatic hydrocarbon solvent is toluene or p-xylene. Preferably, in step a), said stirring is at 60-70° C.

The X-ray powder diffraction pattern of crystalline form III of compound (I) monomesylate of the present disclosure (hereinafter referred to as form III of the present disclosure) shows characteristic peaks at 2theta values of 7.4°±0.2°, 12.9°±0.2° and 19.2°±0.2°.

Furthermore, the X-ray powder diffraction pattern of form III of the present disclosure further shows one or two or three characteristic peaks at 2theta values of 6.5°±0.2°, 21.2°±0.2° and 24.4°±0.2°.

More preferably, the X-ray powder diffraction pattern of form III of the present disclosure further shows one or two or three characteristic peaks at 2theta values of 17.7°±0.2°, 20.7°±0.2° and 26.0°±0.2°.

According to a specific and preferred aspect of the present disclosure, the X-ray powder diffraction pattern of form III of the present disclosure shows characteristic peaks at 2theta values of 7.4°±0.2°, 12.9°±0.2°, 19.2°±0.2°, 6.5°±0.2°, 21.2°±0.2°, 24.4°±0.2°, 17.7°±0.2°, 20.7°±0.2° and 26.0°±0.2°.

Another objective of the present disclosure is to provide a preparation method of form III of the present disclosure, the method comprises either step a) and c) or step b) and c):

a) Adding compound (I) into a mixed solvent of ketones and water, stirring and adding methanesulfonic acid;

b) Adding compound (I) dimesylate into a mixed solvent of alcohols and water, and stirring;

c) Filtering the suspension of step a) or b) and drying the filter cake to obtain form III.

In step a) the volume ratios of said ketones to water varies from 1:1 to 10:1, preferably 3:1 to 4:1. Said ketone can be acetone. The molar ratio of said methanesulfonic acid to compound (I) varies from 1.0:1 to 1.8:1, preferably 1.1:1 to 1.2:1.

Preferably, in step a), said stirring is at 5-50° C., preferably at 20-30° C.

In step b), the volume ratio of said alcohol solvents to water varies from 99:1 to 1:99, preferably 85:15 to 95:5. In step b), said alcohol can be isopropanol. In step b), said stirring is preferably at 25-60° C., more preferably at 45-50° C.

Form I or form II or form III or combination thereof can be used for preparing anti-cancer drugs, particularly preparing drugs for treating chronic lymphocytic leukemia and acute myeloid leukemia.

Another objective of the present disclosure is to provide a pharmaceutical composition comprising a therapeutically effective amount of form I or form II or form III or combination thereof and pharmaceutical adjuvants (pharmaceutically acceptable carrier or excipient). Generally, the pharmaceutical composition or formulation is prepared by mixing or contacting a therapeutically effective amount of form I or form II or form III or combination thereof with one or more pharmaceutical adjuvants, wherein the pharmaceutical composition or the formulation is prepared by a method well known in the pharmaceutical field.

The present disclosure also provides a method for treating or preventing diseases associated SYK, by giving patients a therapeutically and/or prophylactically effective amount of form I, form II, form III or combination thereof.

Due to the implementation of the above technical solution, the present disclosure has the following advantages over the prior art:

The present disclosure provides multiple crystalline forms of entospletinib mesylate, and these forms are more suitable for drug development, and the crystalline forms can be repeatedly prepared by simpler methods.

Figure 1:
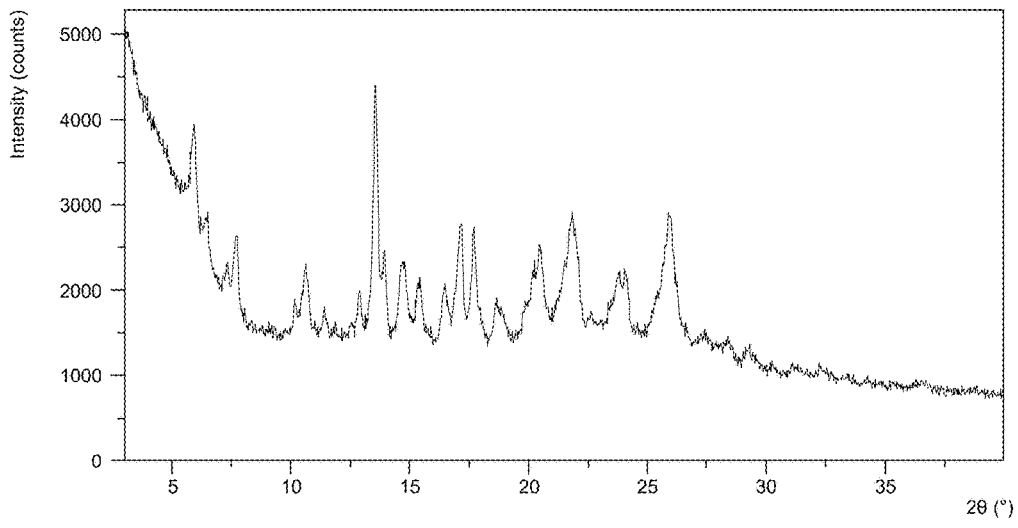
FIG. 1 shows an XRPD pattern of crystalline form I of entospletinib dimesylate in example 1.
Figure 2:
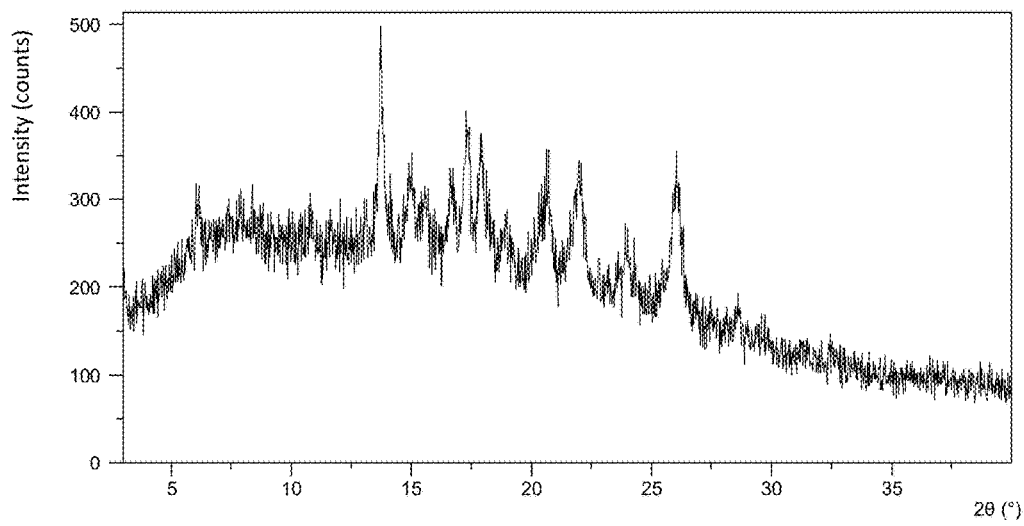
FIG. 2 shows an XRPD pattern of crystalline form I of entospletinib dimesylate in example 2.

The present disclosure provides three novel crystalline forms of compound (I) mesylate, dimesylate form I is referred to as form I of the present disclosure, and its X-ray powder diffraction pattern shows characteristic peaks at 2theta values of 5.9°±0.2°, 13.5°±0.2° and 21.8°±0.2°, and preferably, shows one or two or three characteristic peaks at 2theta values of 25.9°±0.2°, 17.1°±0.2° and 20.4°±0.2°, and more preferably, shows characteristic peaks at 2theta values of 25.9°±0.2°, 17.1°±0.2° and 20.4°±0.2°. Further, the X-ray powder diffraction pattern of form I shows one or two or three characteristic peaks at 2theta values of 10.6°±0.2°, 14.7°±0.2° and 17.7°±0.2°, more preferably, shows characteristic peaks at 2theta values of 10.6°±0.2°, 14.7°±0.2° and 17.7°±0.2°. According to a specific and preferred aspect of the present disclosure, the X-ray powder diffraction pattern of form I shows characteristic peaks at 2theta values of 5.9°±0.2°, 13.5°±0.2°, 21.8°±0.2°, 25.9°±0.2°, 17.1°±0.2°, 20.4°±0.2°, 10.6°±0.2°, 14.7°±0.2° and 17.7°±0.2°. According to one particular example of the present disclosure, the X-ray powder diffraction pattern of form I is substantially as depicted in FIG. 1. In another particular example, the X-ray powder diffraction pattern of form I is substantially as depicted in FIG. 2.

Preferably, form I of the present disclosure is a hydrate.

Figure 3:
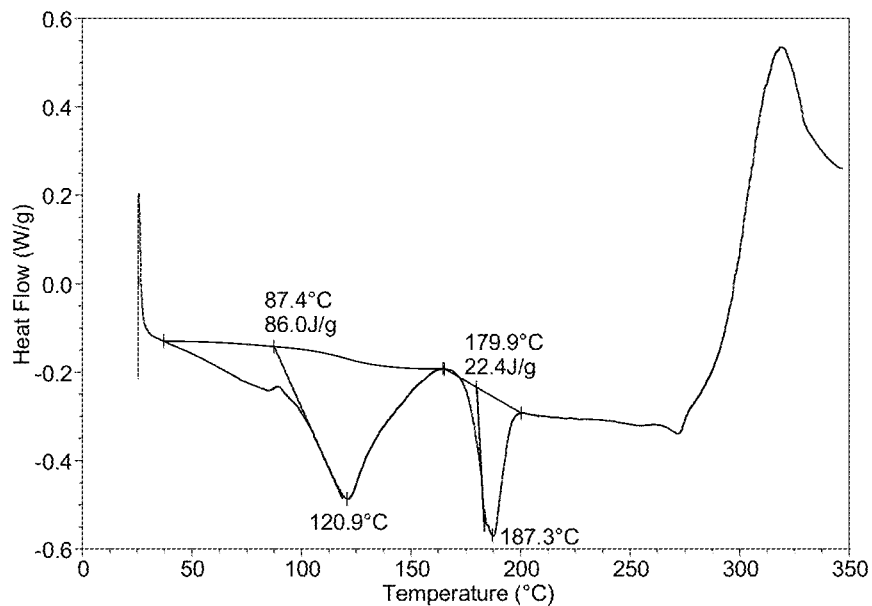
FIG. 3 shows a DSC curve of crystalline form I of entospletinib dimesylate in example 2.

In one specific aspect of the present disclosure, when differential scanning calorimetry is performed, form I of the present disclosure shows an endothermic peak when heated to around 87° C. (onset temperature), and shows another endothermic peak when heated to around 180° C. (onset temperature). The DSC curve is substantially as depicted in FIG. 3.

Figure 4:
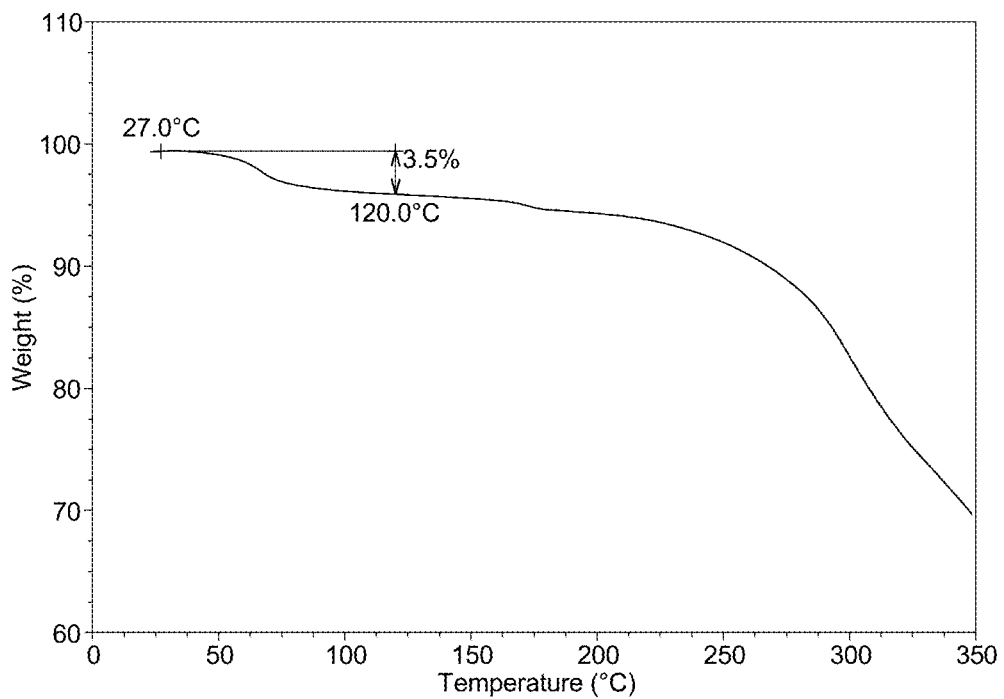
FIG. 4 shows a TGA curve of crystalline form I of entospletinib dimesylate in example 2.

In another specific aspect of the present disclosure, when thermal gravimetric analysis is performed, form I of the present disclosure shows a 3.5% weight loss when heated to 120° C., and the TGA curve is substantially as depicted in FIG. 4.

Figure 5:
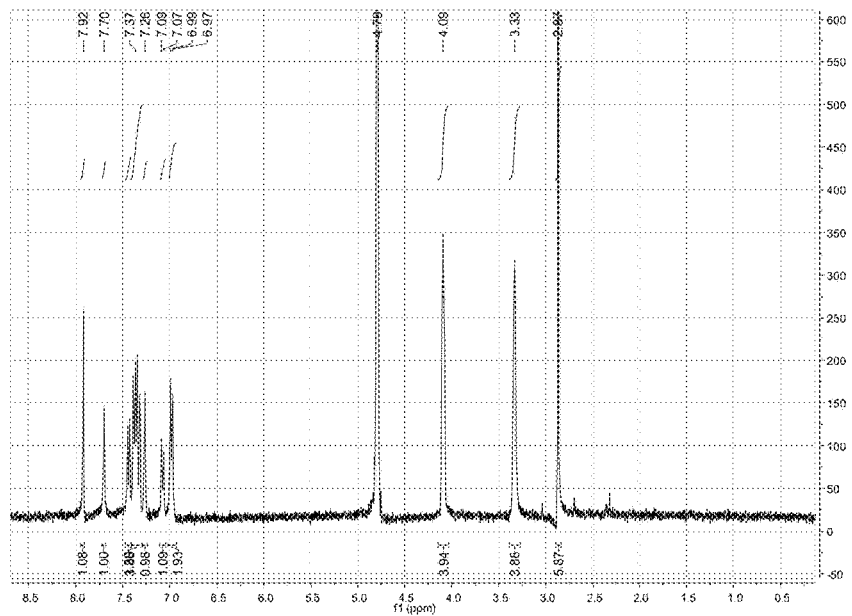
FIG. 5 shows a ¹HNMR spectrum of crystalline form I of entospletinib dimesylate in example 2.

In another specific aspect of the present disclosure, the ¹H NMR data of form I are as follows: ¹H NMR (400 MHz, D$_2$O) δ 7.92 (s, 1H), 7.70 (s, 1H), 7.44 (d, J=8.4 Hz, 1H), 7.36 (dd, J=17.4, 9.7 Hz, 4H), 7.26 (s, 1H), 7.08 (d, J=8.3 Hz, 1H), 6.98 (d, J=8.3 Hz, 2H), 4.09 (s, 4H), 3.33 (s, 4H), 2.87 (s, 6H). The ¹H NMR spectrum is substantially as depicted in FIG. 5.

The preparation method of form I of the present disclosure comprises: a) adding compound (I) dimesylate into a mixed system of multiple organic solvents, and stirring at 5-30° C.; b) filtering the suspension of step a) and drying the filter cake, the obtained solid (usually is pale yellow) is form I of the present disclosure. Among them, said mixed system of multiple organic solvents is preferably a mixed system of alcohol solvents and aromatic hydrocarbon solvents, and the volume ratios of said alcohol solvents to aromatic hydrocarbon solvents varies from preferably 1:1 to 1:5, more preferably 1:2 to 1:3, for example the volume ratio of said alcohol solvents to aromatic hydrocarbon solvents varies from 1:2. Said alcohol solvent can be methanol, said aromatic hydrocarbon solvent can be p-xylene. In step a), said stirring is preferably at 20-30° C., more preferably about 25° C.

Figure 6:
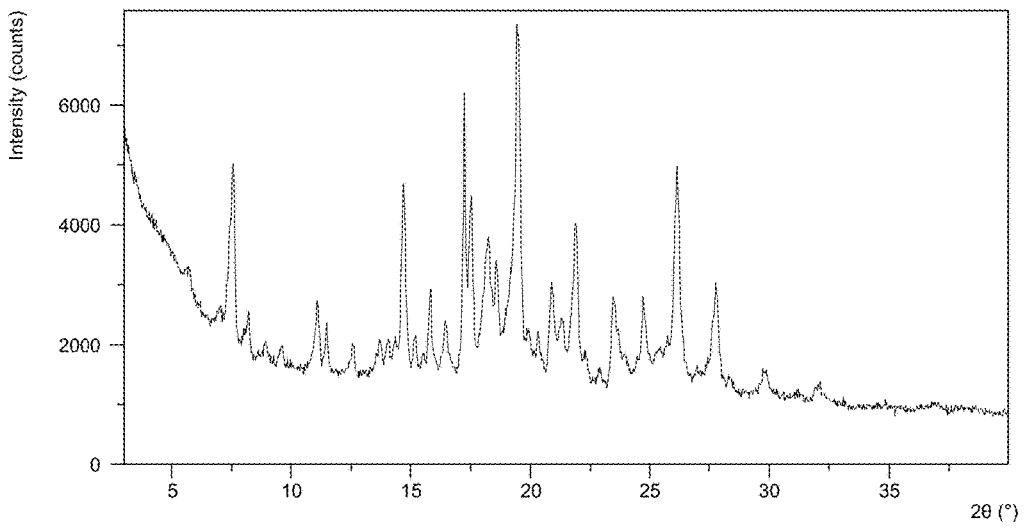
FIG. 6 shows an XRPD pattern of crystalline form II of entospletinib dimesylate in example 3.
Figure 10:
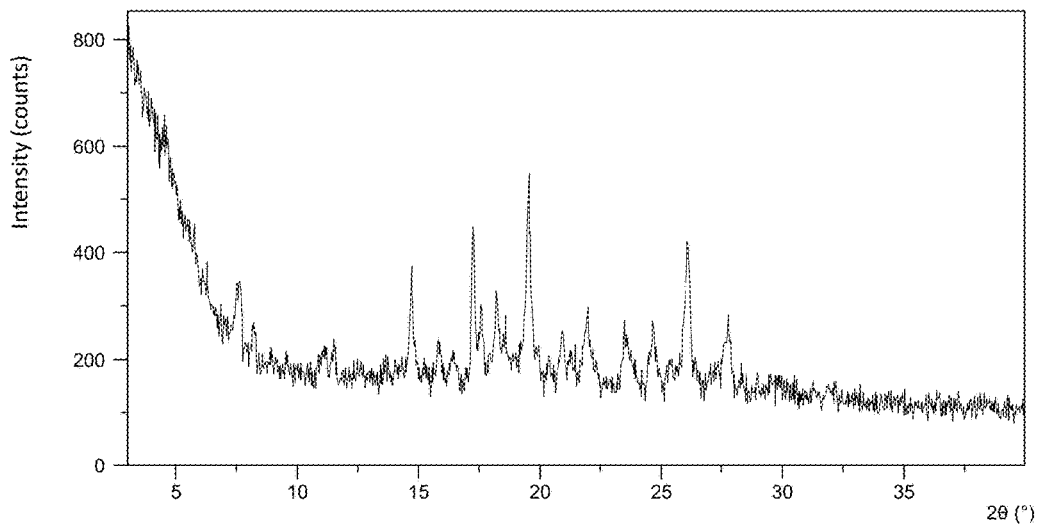
FIG. 10 shows an XRPD pattern of crystalline form II of entospletinib dimesylate in example 4.
Figure 11:
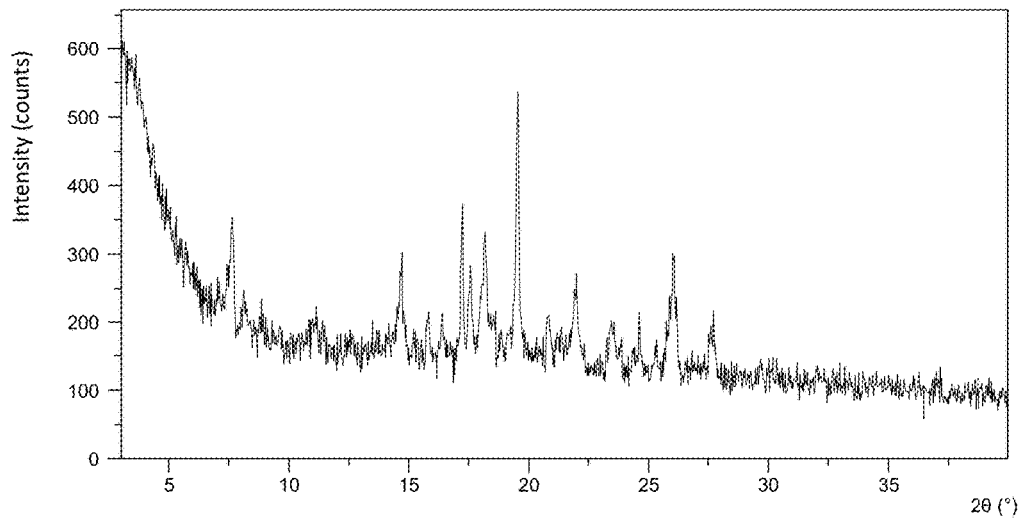
FIG. 11 shows an XRPD pattern of crystalline form II of entospletinib dimesylate in example 5.

Dimesylate form II is referred to as form II of the present disclosure. The X-ray powder diffraction pattern shows characteristic peaks at 2theta values of 15.8°±0.2°, 17.2°±0.2° and 19.5°±0.2°, and preferably, shows one or two or three characteristic peaks at 2theta values of 26.1°±0.2°, 14.7°±0.2° and 21.9°±0.2°, and more preferably, shows characteristic peaks at 2theta values of 26.1°±0.2°, 14.7°±0.2° and 21.9°±0.2°. Further, the X-ray powder diffraction pattern of form II shows one or two or three characteristic peaks at 2theta values of 7.6°±0.2°, 18.2°±0.2° and 27.8°±0.2°, more preferably, shows characteristic peaks at 2theta values of 7.6°±0.2°, 18.2°±0.2° and 27.8°±0.2°. According to a specific and preferred aspect of the present disclosure, the X-ray powder diffraction pattern of form II shows characteristic peaks at 2theta values of 15.8°±0.2°, 17.2°±0.2°, 19.5°±0.2°, 26.1°±0.2°, 14.7°±0.2°, 21.9°±0.2°, 7.6°±0.2°, 18.2°±0.2° and 27.8°±0.2°. According to one particular example of the present disclosure, the X-ray powder diffraction pattern of form II is substantially as depicted in FIG. 6. According to another particular example of the present disclosure, the X-ray powder diffraction pattern of form II is substantially as depicted in FIG. 10. According to another particular example of the present disclosure, the X-ray powder diffraction pattern of form II is substantially as depicted in FIG. 11.

Preferably, form II of the present disclosure is also a hydrate.

Figure 7:
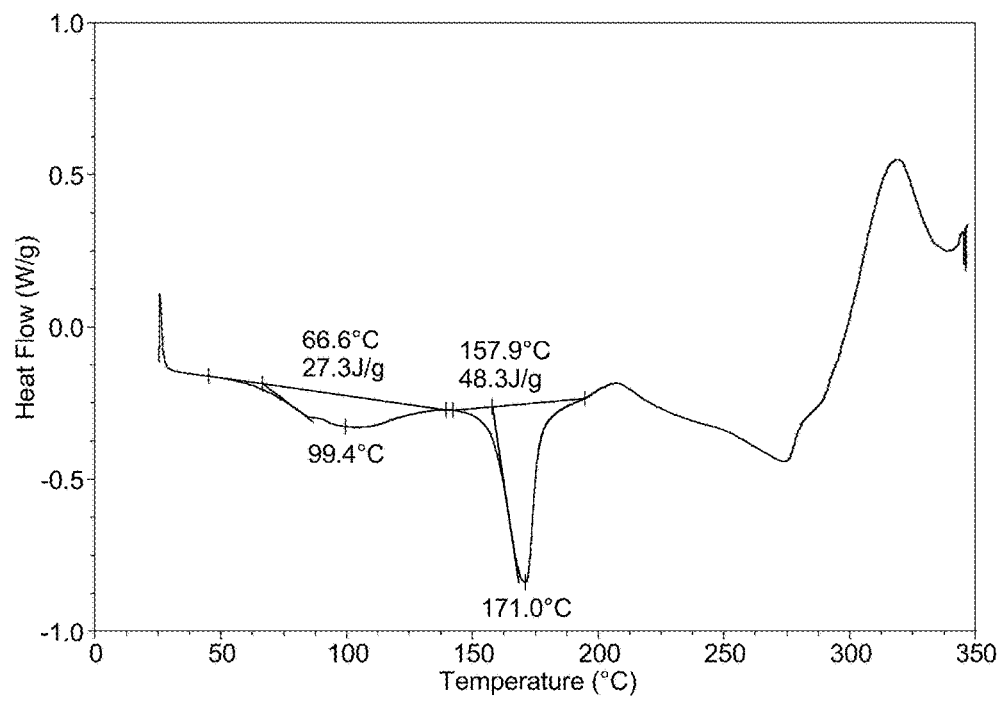
FIG. 7 shows a DSC curve of crystalline form II of entospletinib dimesylate in example 3.

In one specific aspect of the present disclosure, when differential scanning calorimetry is performed, form II of the present disclosure shows an endothermic peak when heated to around 67° C. (onset temperature), and shows another endothermic peak when heated to around 158° C. (onset temperature), and the DSC curve is substantially as depicted in FIG. 7.

Figure 8:
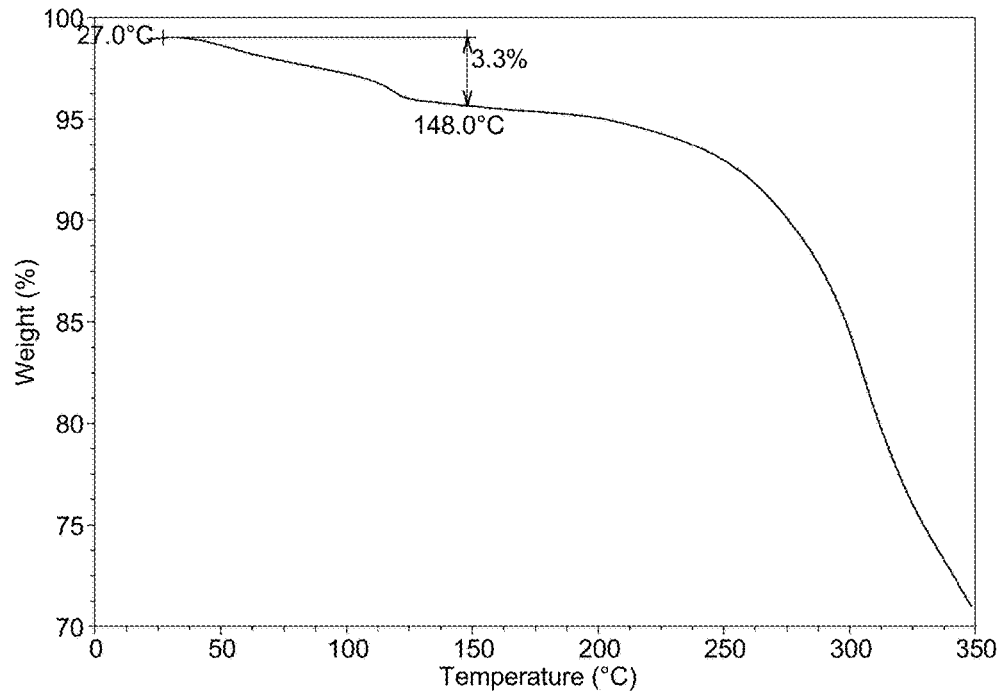
FIG. 8 shows a TGA curve of crystalline form II of entospletinib dimesylate in example 3.

In another specific aspect of the present disclosure, when thermal gravimetric analysis is performed, form II of the present disclosure shows a 3.3% weight loss when heated to 148° C., and the TGA curve is substantially as depicted in FIG. 8.

Figure 9:
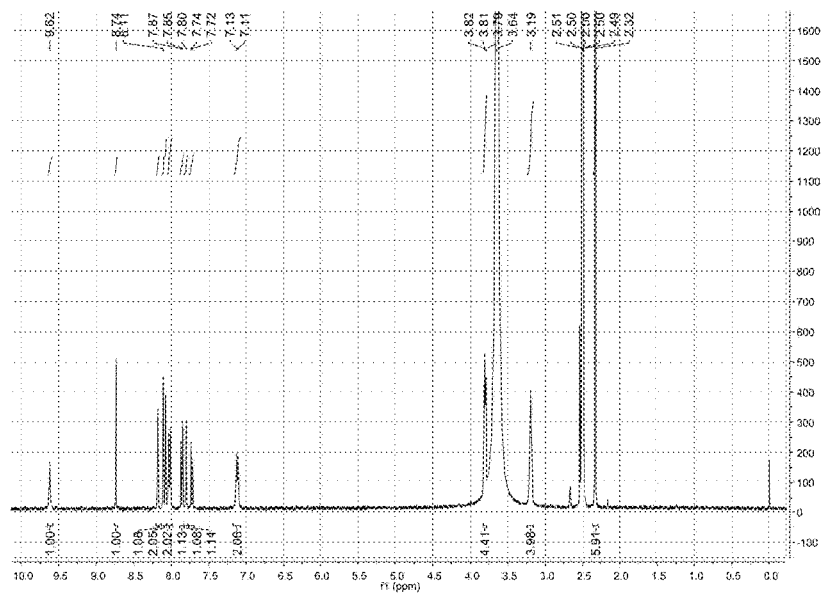
FIG. 9 shows a ¹HNMR spectrum of crystalline form II of entospletinib dimesylate in example 3.

In another specific aspect of the present disclosure, the $^1$H NMR data of form II are as follows: $^1$H NMR (400 MHz, DMSO) δ 9.62 (s, 1H), 8.74 (s, 1H), 8.18 (s, 1H), 8.13-8.06 (m, 2H), 8.02 (d, J=9.0 Hz, 2H), 7.86 (d, J=8.6 Hz, 1H), 7.80 (s, 1H), 7.73 (d, J=8.5 Hz, 1H), 7.12 (d, J=8.5 Hz, 2H), 3.83-3.78 (m, 4H), 3.19 (s, 4H), 2.32 (s, 6H). The $^1$H NMR spectrum is substantially as depicted in FIG. 9.

The present disclosure further provides preparation method of form II, and the method comprises: a) adding compound (I) dimesylate into one or more aromatic hydrocarbon solvents, and stirring at 40-80° C.; b) filtering the suspension of step a) and drying the filter cake. The obtained solid (usually is pale yellow) is crystalline form II. Said aromatic hydrocarbon solvent is preferably toluene or p-xylene. Said stirring is preferably at 60-70° C.

Form I and form II of compound (I) dimesylate of the present disclosure have good stability, low hygroscopicity and suitable particle sizes. The preparation process is simple and can be repeated and scaled up. Compared with prior form 3 and prior form 7, form I and form II of the present disclosure are more suitable for industrial production and application.

Monomesylate form III is referred to as form III of the present disclosure, wherein the X-ray powder diffraction pattern shows characteristic peaks at 2theta values of 7.4°±0.2°, 12.9°±0.2° and 19.2°±0.2°. Further, the X-ray powder diffraction pattern of form III of the present disclosure preferably shows one or two or three characteristic peaks at 2theta values of 6.5°±0.2°, 21.2°±0.2° and 24.4°±0.2°, and more preferably, shows characteristic peaks at 2theta values of 6.5°±0.2°, 21.2°±0.2° and 24.4°±0.2°. Furthermore, the X-ray powder diffraction pattern of form III of the present disclosure further shows one or two or three characteristic peaks at 2theta values of 17.7°±0.2°, 20.7°±0.2° and 26.0°±0.2°, and more preferably, shows characteristic peaks at 2theta values of 17.7°±0.2°, 20.7°±0.2° and 26.0°±0.2°.

Figure 12:
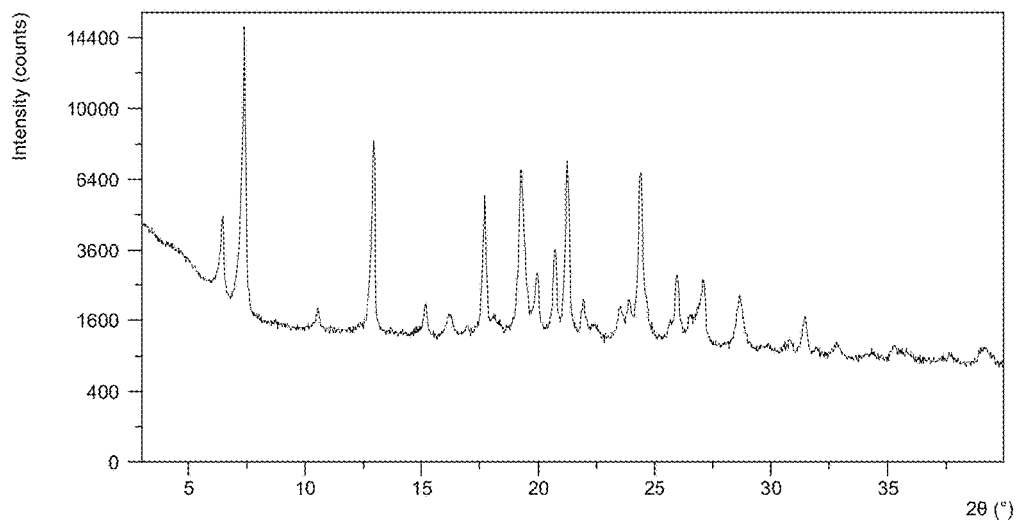
FIG. 12 shows an XRPD pattern of crystalline form III of entospletinib monomesylate in example 6.
Figure 16:
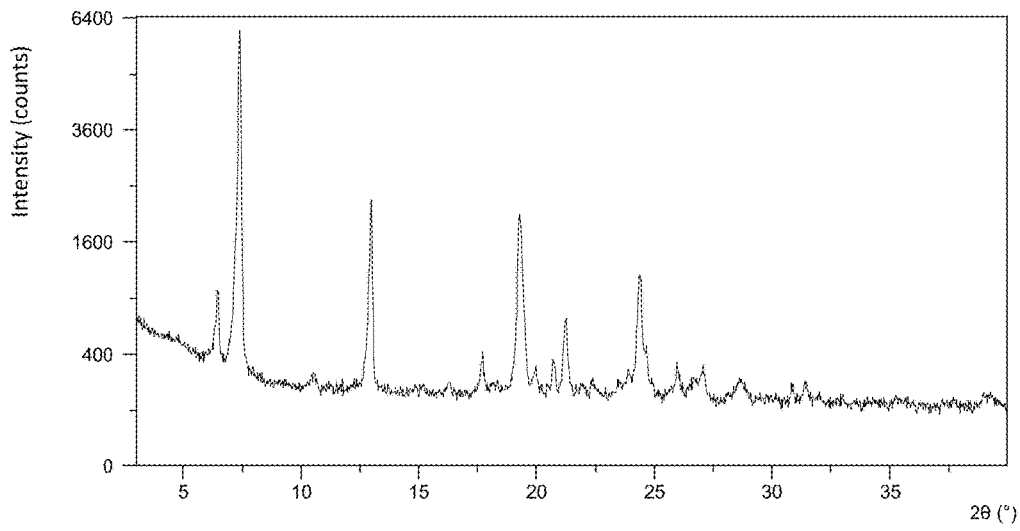
FIG. 16 shows an XRPD pattern of crystalline form III of entospletinib monomesylate in example 7.

According to a specific and preferred aspect of the present disclosure, the X-ray powder diffraction pattern of form III shows characteristic peaks at 2theta values of 7.4°±0.2°, 12.9°±0.2°, 19.2°±0.2°, 6.5°±0.2°, 21.2°±0.2°, 24.4°±0.2°, 17.7°±0.2°, 20.7°±0.2°, 26.0°±0.2°. According to one particular example of the present disclosure, the X-ray powder diffraction pattern of form III is substantially as depicted in FIG. 12. According to another particular example of the present disclosure, the X-ray powder diffraction pattern of form III is substantially as depicted in FIG. 16.

Figure 13:
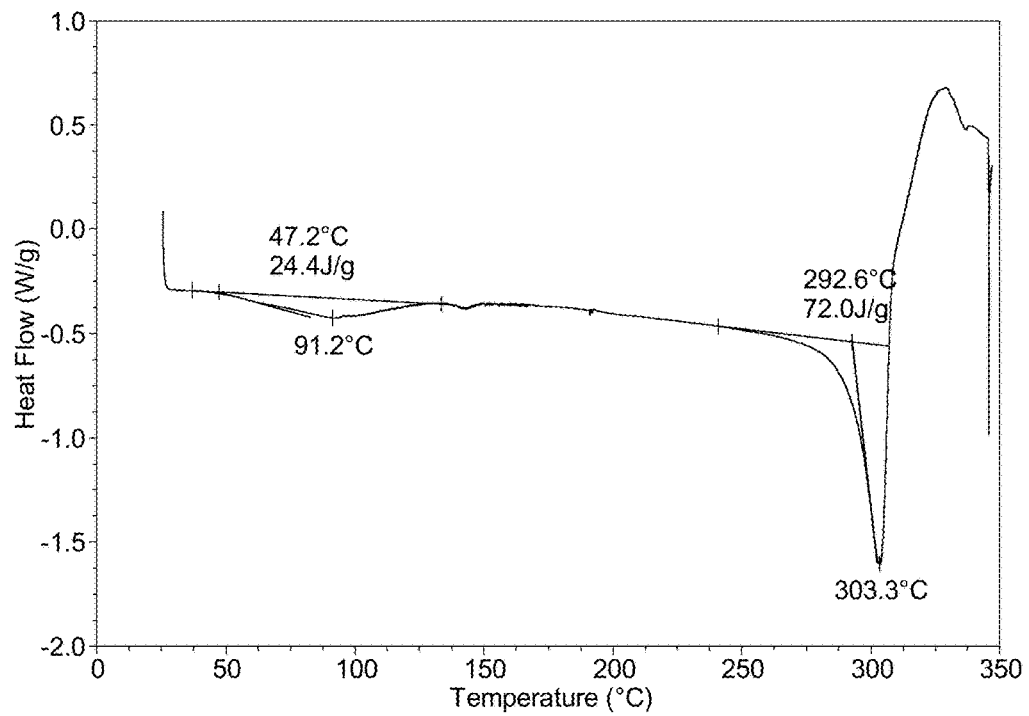
FIG. 13 shows a DSC curve of crystalline form III of entospletinib monomesylate in example 6.
Figure 17:
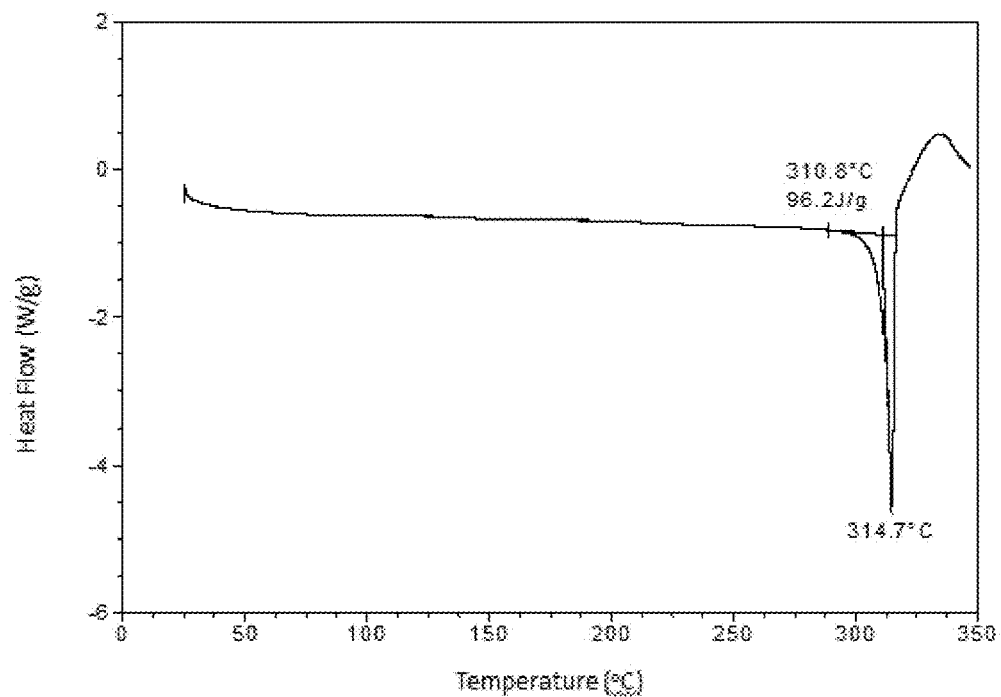
FIG. 17 shows a DSC curve of crystalline form III of entospletinib monomesylate in example 7.

In one specific example of the present disclosure, when differential scanning calorimetry is performed, form III of the present disclosure shows an endothermic peak when heated to around 293° C. (onset temperature), and the DSC curve is substantially as depicted in FIG. 13. In another specific example, when differential scanning calorimetry is performed, form III of the present disclosure shows an endothermic peak when heated to around 311° C. (onset temperature), and the DSC curve is substantially as depicted in FIG. 17.

Figure 14:
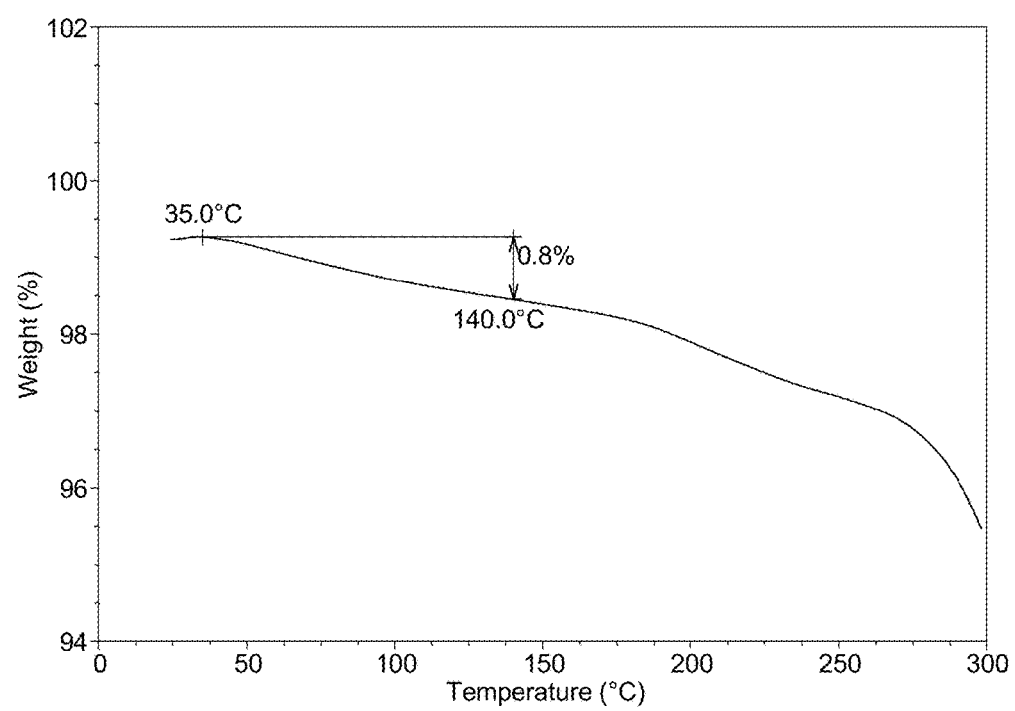
FIG. 14 shows a TGA curve of crystalline form III of entospletinib monomesylate in example 6.
Figure 18:
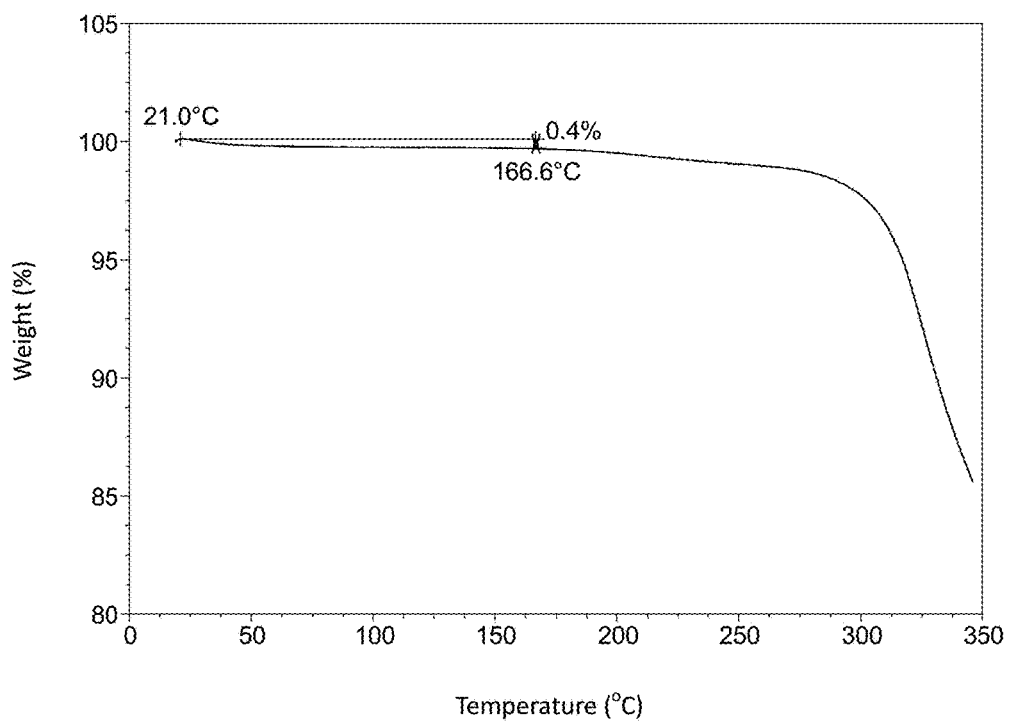
FIG. 18 shows a TGA curve of crystalline form III of entospletinib monomesylate in example 7.

In one specific example of the present disclosure, when thermal gravimetric analysis is performed, form III of the present disclosure shows 0.8% weight loss when heated to around 140° C., and the TGA curve is substantially as depicted in FIG. 14. In another specific example, when thermal gravimetric analysis is performed, form III of the present disclosure shows a 0.4% weight loss when heated to around 167° C., and the TGA curve is substantially as depicted in FIG. 18.

In a particular example of the present disclosure, form III of the present disclosure is an anhydrate.

Figure 15:
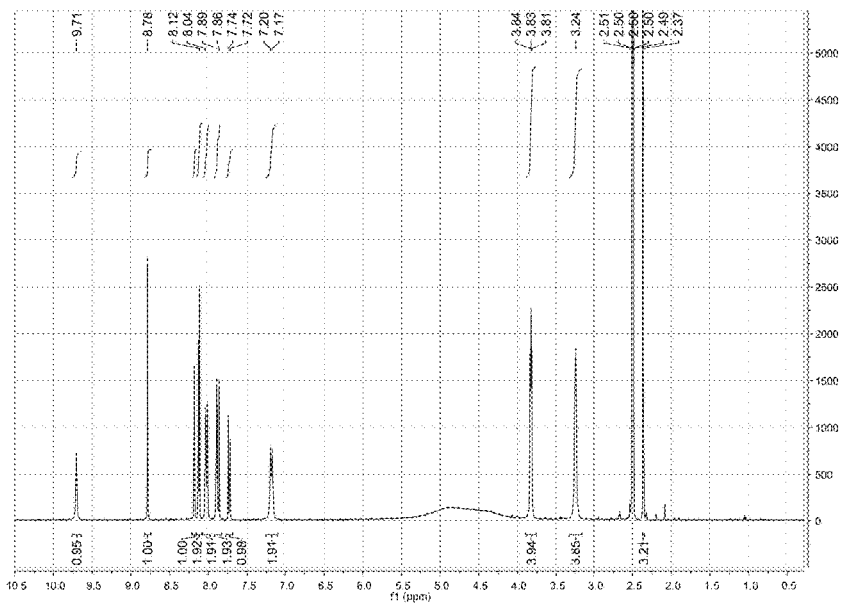
FIG. 15 shows a ¹HNMR spectrum of crystalline form III of entospletinib monomesylate in example 6.

In a particular example of the present disclosure, the $^1$H NMR data of form III are as follows: $^1$H NMR (400 MHz, DMSO) δ 9.71 (s, 1H), 8.78 (s, 1H), 8.18 (s, 1H), 8.12 (dd, J=5.3, 1.1 Hz, 2H), 8.03 (d, J=8.9 Hz, 2H), 7.93-7.84 (m, 2H), 7.73 (dd, J=8.5, 1.3 Hz, 1H), 7.19 (d, J=8.5 Hz, 2H), 3.89-3.76 (m, 4H), 3.24 (s, 4H), 2.37 (s, 3H). The $^1$H NMR spectrum is substantially as depicted in FIG. 15.

Another objective of the present disclosure is to provide preparation methods of form III, wherein the method comprises either step a) and c) or step b) and c):

a) Adding compound (I) into a mixed solvent of ketones and water, adding methanesulfonic acid while stirring, then stirring is continued;

b) Adding compound (I) dimesylate into a mixed solvent of alcohols and water, and stirring;

c) Filtering the suspension of step a) or b) and drying the filter cake to obtain Form III.

Furthermore, in step a) the volume ratio of said ketones to water varies from 1:1 to 10:1, preferably 3:1 to 4:1. Said ketone can be acetone. The molar ratio of said methanesulfonic acid to compound (I) varies from 1.0:1 to 1.8:1, preferably 1.1:1 to 1.2:1. In step a), said stirring is preferably at 5-50° C., more preferably at 20-30° C., most preferably at 25° C.

Furthermore, in step b), the volume ratio of said alcohol solvents to water varies from 99:1 to 1:99, preferably 85:15 to 95:5. In step b), said alcohol can be isopropanol. In step b), said stirring is preferably at 25-60° C., more preferably at 45-50° C.

Form III of compound (I) monomesylate of the present disclosure has good stability, high crystallinity, and low hygroscopicity. Compared with prior form 3, Form III has better stability in the presence of water or at a high-humidity condition. In addition, form III has obvious advantages in production and repeatability. Form III is more suitable for drug development compared with prior form 3.

In some examples, form I, form II and form III of the present disclosure are pure, single forms and substantially free of any other crystalline forms. In the present disclosure, when "substantially free of" is used for describing a novel crystalline form, it means that the content of other crystalline forms in the novel crystalline form is less than 20% (w/w), specifically less than 10% (w/w), more specifically less than 5% (w/w) and further more specifically less than 1% (w/w).

Three crystalline forms with advantages shown above were surprisingly discovered in the present disclosure, which provides a new and better choice for pharmaceutical formulations of compound (I), and is very important significance for drug development.

According to the present disclosure, compound (I) and/or a salt thereof as a raw material can be a solid (crystalline or amorphism), a semisolid, wax or oil form. Preferably, compound (I) and/or a salt thereof as a raw material is a solid.

According to the present disclosure, said "stirring" is accomplished with the routine methods in this field, such as magnetic stirring or mechanical stirring; the stirring speed is 50-1800 rpm, and preferably, 300-900 rpm.

Unless otherwise specified, said "drying" may be conducted at room temperature or higher temperature. The drying temperature is from room temperature to 60° C., or to 40° C., or to 50° C. The drying time may be 2-48 hours, or overnight. Drying may be conducted in a fume hood, a blast drying oven or a vacuum drying oven.

In the present disclosure, "Crystal" or "Crystalline Form" refers to the crystal or the crystal form being identified by the X-ray diffraction pattern shown herein. The scientists in this field are able to understand that physical and chemical properties discussed herein can be characterized, wherein the experimental errors depend on the conditions of instruments, the sample preparations and the purity of samples. In particular, the scientists in this field generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, generally, the experimental errors of the peak angles are 5% or less, so such errors shall be considered and generally the allowed errors are ±0.2°. In addition, due to the effect of the experimental factors including sample height, peak angles may have an overall shifting; generally, certain shifting is allowed. Hence, the scientists in this field may understand that, it is unnecessary that the X-ray diffraction pattern of a crystal form in the present invention should be exactly the same with X-ray diffraction patterns of the example shown herein. Any crystal forms whose X-ray diffraction patterns have the same or similar characteristic peaks should be within the scope of the present invention. The scientists in this field can compare the patterns shown in the present invention with that of an unknown crystal form in order to identify whether these two groups of patterns reflect the same or different crystal forms.

"Crystalline form" and "polymorphic form" as well as other related terms in the present invention refer to the solid compounds whose crystal structure is being in a special crystal form state. The difference in the physical and chemical properties of the polymorphs may be embodied in storage stability, compressibility, density, dissolution rate, etc. In extreme cases, the difference in solubility or dissolution rate may result in inefficient drugs, even developing toxicity.

In addition, the three forms provided by the present disclosure can be used for preparing drugs inhibiting SYK.

The term "SYK" of the present disclosure is spleen tyrosine kinase, which is a member of protein tyrosine kinase (PTK) family, and is a kind of non-receptor tyrosine kinase and mainly in the spleen, thymus and lungs.

Further, the present disclosure is to provide a pharmaceutical composition comprising a therapeutically effective amount of form I or form II or form III or their mixture and pharmaceutical adjuvants (pharmaceutically acceptable carrier or excipient). Generally, the pharmaceutical composition or formulation is prepared by mixing or contacting a therapeutically effective amount of form I or form II or form III or a mixture thereof with one or more pharmaceutical adjuvants, wherein the pharmaceutical composition or the formulation is prepared by a method well known in the pharmacy field. According to one specific and preferred aspect, the pharmaceutical composition is in the form of a pharmaceutical formulation, and the form of the pharmaceutical formulation is a tablet, a capsule, a suspension, a disintegrating tablet, an immediate release, sustained-release or controlled-release tablet. Preferably, the drug has the effects of preventing or treating the diseases selected from breast cancer, stomach cancer, lymphoma, rectal cancer, pancreatic cancer, liver cancer, leukemia, malignant epithelial tumors, and tumor metastasis, multiple sclerosis, immune diseases, allergic diseases, atherosclerosis, gastrointestinal dysfunction, idiopathic thrombocytopenic purpura, Wiskott-aldrich syndrome and systemic lupus erythematosus.

The term "effective amount" or "therapeutically effective amount" as used herein means that amount of an active compound that elicits the biological or medicinal response in a tissue, system, animal or human that is being sought by a researcher, veterinarian, medical doctor, or other clinician.

As used herein, the term "treatment" refers to one or more of the following: (1) Preventing disease, for example, preventing the disease, illness or disorder in an individual who may be suffering from a disease, illness or disorder but not suffering from or displaying a lesion or symptom of the disease, (2) Inhibiting the disease, for example, inhibiting the disease, illness or disorder in an individual who is suffering from or displaying a lesion or symptom of the disease, illness or disorder, and (3) Improving the disease, for example, improving the disease, illness or disorder in an individual who is suffering from or displaying a lesion or symptom of the disease, illness or disorder (that is to reverse the lesion and/or symptoms), for example, reducing the severity of the disease.

In addition, the pharmaceutical composition provided by the present disclosure can also contain other medicinal crystalline forms and a morphism of 6-(1H-indazole-6-yl))-N-[4-(4-morpholinyl)) phenyl] imidazo [1, 2-a]pyrazine-8-amine or its mesylate besides said crystalline forms of the present disclosure. Optionally, the crystalline forms of the present disclosure can be applied as a separate active agent, or they can be applied in combination with other active agents, including other compounds which have the same or similar therapeutic activity and are determined to be safe and effective in combination with such combinations. In a particular example, Co-administration of two (or more) active agents can reduce the dosage of each active agent, so that the side effects can be reduced. The co-administration include but is not limited to those disclosed in the specification of prior art US20150038505 A1.

The pharmaceutical composition can be obtained by methods known to those skilled in the art in the prior art. When preparing the pharmaceutical composition, the crystalline forms of the pharmaceutical composition is mixed with one or more pharmaceutically acceptable excipients, and mixed with one or more other active pharmaceutical ingredients. For example, the tablet, the capsule and the granule can be prepared through processes of mixing, granulating, tableting or filling capsules. The powder is prepared by mixing active pharmaceutical ingredients and excipients which are ground into a proper size. The solution and the syrup can be prepared by dissolving the active pharmaceutical ingredients in a properly flavored water or aqueous solution. The suspension can be prepared by dispersing the active pharmaceutical ingredients in pharmaceutically acceptable carriers.

It should be noted that the number and the range of number should not be narrowly understood as a value or numerical value range. It should be understood by those skilled in the art that the specific numerical value can be floated according to the specific technical environment on the basis that the spirit and principle of the present disclosure are not depart from the spirit and principle of the present disclosure. In the present disclosure, the number of floating ranges which can be expected by one of skilled in the art is represented by the term "about".

The present disclosure will be further explained by the specific examples and the specific examples are not intended to limit the scope of the present disclosure. The skilled in the art can make improvements to the process of preparation and the used instruments within the scope of the claims, and those improvements should be considered as falling into the scope of the present disclosure. Therefore, the protective scope of the present disclosure patent should be defined by the claims.

In the following examples, the test is generally implemented according to a conventional condition or a condition that manufacturer recommends.

The abbreviations used in the present disclosure are explained as follows:
XRPD: X-ray Powder Diffraction
DSC: Differential Scanning calorimetry
TGA: Thermal Gravimetric Analysis
DVS: Dynamic Vapor Sorption
$^1$H NMR: $^1$H Nuclear Magnetic Resonance
PLM: Polarized Light microscopy
PSD: Particle Size Distribution X-ray powder diffraction pattern in the present disclosure is acquired by a Panalytical Empyrean X-ray powder diffractometer. The parameters of the X-ray powder diffraction method of the present disclosure are as follows:
X-ray Reflection: Cu, Kα
Kα1 (Å): 1.540598. Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure are acquired by a TA Q2000. The parameters of the differential scanning calorimetry (DSC) method of the present disclosure are as follow:
Heating rate: 10° C./min
Purge gas: nitrogen Thermal gravimetric analysis (TGA) data in the present disclosure are acquired by a TA Q5000. The parameters of the thermal gravimetric analysis (TGA) method of the present disclosure are as follows:
Heating rate: 10° C./min
Purge gas: nitrogen Dynamic Vapor Sorption (DVS) is measured via a SMS (Surface Measurement Systems Ltd.) intrinsic DVS. Its control software is DVS-Intrinsic control software, and its analysis software is DVS-Intrinsic Analsis software. Typical Parameters for DVS test are as follows:
Temperature: 25° C.
Gas and flow rate: $N_2$, 200 mL/min
dm/dt: 0.002%/min
RH range: 0% RH to 95% RH Proton nuclear magnetic resonance spectrum data ($^1$HNMR) is collected from a Bruker Avance II DMX 400M HZ NMR spectrometer. 1-5 mg of sample was weighed, dissolved in 0.5 mL deuterated dimethyl sulfoxide or deuterated water to obtain a solution with the concentration of 2-10 mg/mL.

The particle size distribution test in the present disclosure is acquired by the S3500 laser particle size analyzer of Microtrac. Microtrac S3500 is equipped with the Sample Delivery Controller. The test is carried out by wet process, and the dispersion medium is Isopar G. The parameters are as follow:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency:: Trans | Residuals: Enabled |
| Particle refractive index: 1.5 | Flow rate: 60%* |
| Particle shape: Irregularity | Filtration: Enabled |
| Ultrasonication power: 30 W | Ultrasonication time: 30 s |

*Flow rate 60% is 60% of 65 mL/s.

The abbreviations used in the present disclosure are explained as follows:
D10: The D10 describes the diameter where 10% of the distribution has a smaller particle size.
D50: The D50 describes the diameter where 50% of the distribution has a smaller particle size. The median is also called D50.
D90: The D90 describes the diameter where 90% of the distribution has a smaller particle size. Unless otherwise specified, the following examples were conducted at room temperature.

In the following examples, entospletinib and compound (I) have the same meaning.

Amorphous entospletinib dimesylate or prior form 7 may be prepared by known method in prior art.

EXAMPLE 1 PREPARATION OF FORM I OF THE PRESENT DISCLOSURE 12.2 mg of entospletinib dimesylate (amorphous) was added into a 1.5 mL glass vial, then 0.6 mL of methanol/p-xylene (1:2, v/v) was added to the vial. The obtained solution was stirred for 2 weeks at 5° C. The suspension was filter and the filter cake was dried to obtain a pale yellow solid, which was form I. The XRPD data of the solid prepared in this example are listed in Table 1, and the XRPD pattern is displayed in FIG. 1.

TABLE 1

| 2theta | d spacing | Intensity % |
|---|---|---|
| 5.96 | 14.82 | 75.26 |
| 7.71 | 11.46 | 52.87 |
| 10.67 | 8.29 | 36.05 |
| 11.41 | 7.75 | 22.19 |
| 12.94 | 6.84 | 26.12 |
| 13.51 | 6.56 | 98.03 |
| 13.96 | 6.35 | 40.28 |
| 14.82 | 5.98 | 38.78 |
| 15.42 | 5.75 | 33.68 |
| 16.46 | 5.39 | 30.61 |
| 17.13 | 5.18 | 53.01 |
| 17.73 | 5.00 | 48.74 |
| 18.75 | 4.73 | 23.26 |
| 20.55 | 4.32 | 42.48 |
| 21.80 | 4.08 | 58.91 |
| 24.06 | 3.70 | 37.86 |
| 25.89 | 3.44 | 53.71 |
| 28.42 | 3.14 | 13.81 |
| 29.29 | 3.05 | 11.29 |
| 31.53 | 2.84 | 2.35 |

EXAMPLE 2 PREPARATION OF FORM I OF THE PRESENT DISCLOSURE 14.5 mg of entospletinib dimesylate (amorphous) was added into a 1.5 mL glass vial, then 0.6 mL of methanol/p- xylene (1:2, v/v) was added to the vial. The obtained solution was stirred for 2 days at room temperature. The suspension was filter and the filter cake was dried to obtain a pale yellow solid, which was form I. The XRPD data of the solid prepared in this example are listed in Table 2, and the XRPD pattern is displayed in FIG. 2. The DSC curve is displayed in FIG. 3. The TGA curve is displayed in FIG. 4. The $^1$H NMR spectra is displayed in FIG. 5

TABLE 2

| 2theta | d spacing | Intensity % |
|---|---|---|
| 5.93 | 14.91 | 23.56 |
| 10.63 | 8.32 | 16.33 |
| 13.58 | 6.52 | 100.00 |
| 14.73 | 6.01 | 40.01 |
| 15.41 | 5.75 | 39.15 |
| 16.52 | 5.37 | 36.75 |
| 17.19 | 5.16 | 66.15 |
| 17.69 | 5.01 | 60.08 |
| 18.64 | 4.76 | 26.44 |
| 20.43 | 4.35 | 48.49 |
| 21.84 | 4.07 | 57.17 |
| 23.75 | 3.75 | 32.83 |
| 25.85 | 3.45 | 62.39 |
| 28.33 | 3.15 | 14.34 |
| 29.23 | 3.06 | 12.31 |

EXAMPLE 3 PREPARATION OF FORM II OF THE PRESENT DISCLOSURE 19.5 mg of entospletinib dimesylate (prior form 7) was added into a 1.5 mL glass vial, then 1.0 mL of toluene was added to the vial. The obtained solution was stirred for 2 days at 70° C. The suspension was filter and the filter cake was dried to obtain a pale yellow solid, which was form II. The XRPD data of the solid prepared in this example are listed in Table 3, and the XRPD pattern is displayed in FIG. 6. The DSC curve is displayed in FIG. 7. The TGA curve is displayed in FIG. 8. The $^1$H NMR spectra is displayed in FIG. 9.

TABLE 3

| 2theta | d spacing | Intensity % |
|---|---|---|
| 7.57 | 11.68 | 41.95 |
| 11.40 | 7.76 | 14.94 |
| 14.68 | 6.03 | 42.48 |
| 15.76 | 5.62 | 15.46 |
| 16.45 | 5.39 | 8.72 |
| 17.21 | 5.15 | 67.93 |
| 17.55 | 5.05 | 34.15 |
| 18.14 | 4.89 | 39.11 |
| 18.59 | 4.77 | 29.71 |
| 19.54 | 4.54 | 100.00 |
| 20.80 | 4.27 | 19.33 |
| 21.95 | 4.05 | 36.17 |
| 23.47 | 3.79 | 27.56 |
| 24.59 | 3.62 | 27.51 |
| 26.03 | 3.42 | 80.76 |
| 27.67 | 3.22 | 42.48 |
| 28.32 | 3.15 | 4.94 |
| 29.76 | 3.00 | 6.06 |
| 31.99 | 2.80 | 2.14 |

EXAMPLE 4 PREPARATION OF FORM II OF THE PRESENT DISCLOSURE 22.5 mg of entospletinib dimesylate (prior form 7) was added into a 1.5 mL glass vial, then 1.0 mL of p-xylene was added to the vial. The obtained solution was stirred for 2 days at 70° C. The suspension was filter and the filter cake was dried to obtain a pale yellow solid, which was form II. The XRPD data of the solid prepared in this example are listed in Table 4, and the XRPD pattern is displayed in FIG. 10.

TABLE 4

| 2theta | d spacing | Intensity % |
|---|---|---|
| 7.55 | 11.72 | 25.40 |
| 8.15 | 10.85 | 12.30 |
| 10.96 | 8.07 | 9.72 |
| 11.45 | 7.73 | 12.91 |
| 13.62 | 6.50 | 7.57 |
| 14.67 | 6.04 | 50.93 |
| 15.78 | 5.62 | 19.59 |
| 16.36 | 5.42 | 13.42 |
| 17.20 | 5.16 | 72.10 |
| 17.53 | 5.06 | 37.35 |
| 18.17 | 4.88 | 37.10 |
| 18.52 | 4.79 | 27.37 |
| 19.49 | 4.55 | 100.00 |
| 20.87 | 4.26 | 25.70 |
| 21.89 | 4.06 | 35.62 |
| 23.44 | 3.80 | 28.07 |
| 24.63 | 3.61 | 30.14 |
| 26.05 | 3.42 | 72.29 |
| 27.72 | 3.22 | 37.09 |
| 29.76 | 3.00 | 7.93 |
| 31.95 | 2.80 | 4.33 |

EXAMPLE 5 PREPARATION OF FORM II OF THE PRESENT DISCLOSURE 87.5 mg of entospletinib dimesylate (prior form 7) was added into a 3 mL glass vial, then 1.5 mL of toluene was added to the vial. The obtained solution was stirred for 2 days at 70° C. The suspension was filter and the filter cake was dried to obtain a pale yellow solid, which was form II. The XRPD data of the solid prepared in this example are listed in Table 5, and the XRPD pattern is displayed in FIG. 11.

TABLE 5

| 2theta | d spacing | Intensity % |
|---|---|---|
| 7.61 | 11.61 | 38.45 |
| 10.97 | 8.07 | 10.72 |
| 14.68 | 6.03 | 34.25 |
| 15.81 | 5.60 | 15.84 |
| 16.38 | 5.41 | 14.96 |
| 17.21 | 5.15 | 55.70 |
| 17.57 | 5.05 | 34.21 |
| 18.17 | 4.88 | 49.70 |
| 19.53 | 4.55 | 100.00 |
| 20.80 | 4.27 | 18.86 |
| 21.98 | 4.04 | 32.16 |
| 23.45 | 3.79 | 17.70 |
| 24.59 | 3.62 | 19.35 |
| 25.28 | 3.52 | 9.80 |
| 26.02 | 3.42 | 45.77 |
| 27.64 | 3.23 | 18.29 |
| 37.05 | 2.43 | 5.38 |

EXAMPLE 6 PREPARATION OF FORM III OF THE PRESENT DISCLOSURE 30.7 mg of compound (I) (Entospletinib) was added into a 1.5 mL glass vial, then 0.6 mL of acetone/water (4:1, v/v) was added to the vial. 5.8 μL of methanesulfonic acid (99%) was added to the above solution under magnetic stirring, and the obtained solution was stirred for 28 hours at 25° C. The suspension was filter and the filter cake was dried to obtain a pale yellow solid, which was form III.

The XRPD data of the solid prepared in this example are listed in Table 6, and the XRPD pattern is displayed in FIG. 12. The DSC curve is displayed in FIG. 13. The TGA curve is displayed in FIG. 14. The $^1$H NMR spectra is displayed in FIG. 15.

TABLE 6

| 2theta | d spacing | Intensity % |
|---|---|---|
| 6.44 | 13.72 | 18.72 |
| 7.38 | 11.98 | 100.00 |
| 10.54 | 8.39 | 3.37 |
| 12.94 | 6.84 | 52.02 |
| 15.16 | 5.84 | 5.20 |
| 16.20 | 5.47 | 3.48 |
| 17.69 | 5.01 | 33.92 |
| 19.24 | 4.61 | 43.16 |
| 19.93 | 4.45 | 12.83 |
| 20.70 | 4.29 | 18.84 |
| 21.23 | 4.18 | 47.17 |
| 21.92 | 4.06 | 7.39 |
| 23.48 | 3.79 | 6.21 |
| 23.88 | 3.73 | 7.33 |
| 24.37 | 3.65 | 43.67 |
| 25.95 | 3.43 | 13.62 |
| 26.50 | 3.36 | 5.21 |
| 27.08 | 3.29 | 12.77 |
| 28.64 | 3.12 | 9.66 |
| 30.83 | 2.90 | 1.82 |
| 31.41 | 2.85 | 5.63 |
| 32.80 | 2.73 | 1.53 |
| 35.23 | 2.55 | 1.79 |
| 37.60 | 2.39 | 0.51 |

EXAMPLE 7 PREPARATION OF FORM III OF THE PRESENT DISCLOSURE 100.0 mg of compound (I) (Entospletinib) was added into a 5.0 mL glass vial, then 1.5 mL of acetone/water (4:1, v/v) was added to the vial. 18.9 µL of methanesulfonic acid (99%) was added to the above solution under magnetic stirring, and the obtained solution was stirred for 28 hours at 25° C. The suspension was filter and the filter cake was dried to obtain a pale yellow solid, which was form III. The XRPD data of the solid prepared in this example are listed in Table 7, and the XRPD pattern is displayed in FIG. 16. The DSC curve is displayed in FIG. 17. The TGA curve is displayed in FIG. 18.

TABLE 7

| 2theta | d spacing | Intensity % |
|---|---|---|
| 6.44 | 13.72 | 10.82 |
| 7.38 | 11.98 | 100.00 |
| 10.48 | 8.44 | 1.20 |
| 12.94 | 6.84 | 35.48 |
| 16.27 | 5.45 | 0.82 |
| 17.68 | 5.02 | 4.01 |
| 19.24 | 4.61 | 30.56 |
| 19.93 | 4.46 | 2.45 |
| 20.71 | 4.29 | 3.17 |
| 21.23 | 4.18 | 9.26 |
| 24.34 | 3.66 | 17.93 |
| 25.94 | 3.44 | 3.28 |
| 27.05 | 3.30 | 2.91 |
| 28.65 | 3.12 | 1.69 |
| 30.83 | 2.90 | 0.98 |
| 31.39 | 2.85 | 1.46 |

Figure 19:
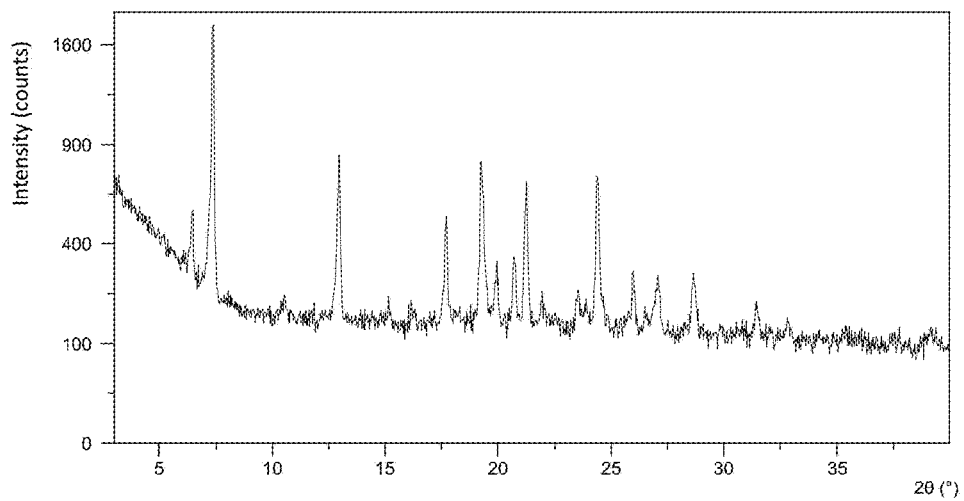
FIG. 19 shows an XRPD pattern of crystalline form III of entospletinib monomesylate in example 8.

EXAMPLE 8 PREPARATION OF FORM III OF THE PRESENT DISCLOSURE 7.5 mg of compound (I) (Entospletinib) was added into a 1.5 mL glass vial, then 0.35 mL of isopropanol/water (89:11, v/v) was added. The obtained solution was stirred for 6 days at 50° C. The suspension was filter and the filter cake was dried to obtain a pale yellow solid, which was form III. The XRPD data of the solid prepared in this example are listed in Table 8, and the XRPD pattern is displayed in FIG. 19.

TABLE 8

| 2theta | d spacing | Intensity % |
|---|---|---|
| 6.44 | 13.71 | 16.35 |
| 7.38 | 11.98 | 100.00 |
| 10.43 | 8.48 | 2.65 |
| 12.94 | 6.84 | 45.05 |
| 16.19 | 5.47 | 2.78 |
| 17.70 | 5.01 | 25.34 |
| 19.23 | 4.61 | 45.36 |
| 19.94 | 4.45 | 11.16 |
| 20.71 | 4.29 | 14.57 |
| 21.25 | 4.18 | 36.56 |
| 21.94 | 4.05 | 5.49 |
| 23.50 | 3.79 | 6.51 |
| 24.37 | 3.65 | 39.45 |
| 25.94 | 3.43 | 11.72 |
| 27.10 | 3.29 | 10.04 |
| 28.66 | 3.11 | 10.76 |
| 31.45 | 2.84 | 5.63 |
| 32.83 | 2.73 | 2.17 |

EXAMPLE 9 HYGROSCOPICITY OF FORM III

Figure 20:
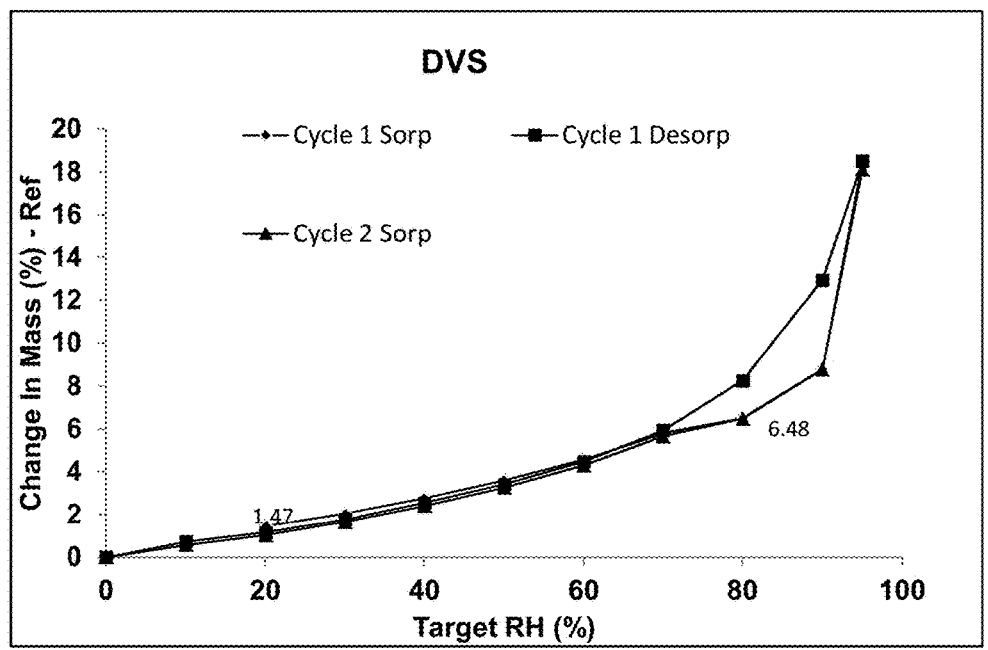
FIG. 20 shows a DVS plot of crystalline form III of entospletinib monomesylate in example 9.
Figure 21:
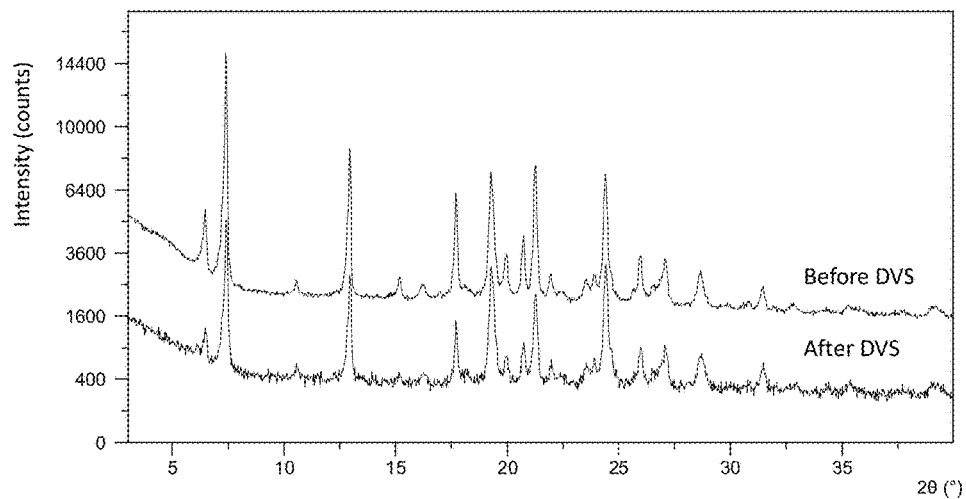
FIG. 21 shows an XRPD overlay pattern of form III in example 9 before and after DVS experiment.

Hygroscopicity of form III was measured in dynamic vapor sorption (DVS) instrument using 7.34 mg of form III obtained from example 6. The DVS plot is shown in FIG. 20, and the weight gain of form III at 80% RH is 6.48%. The solid after DVS was collected for XRPD test, and the XRPD result is shown in FIG. 21, which indicates form III doesn't change during DVS test.

Form III of the present disclosure has a weight gain of 6.48% at 80% RH, while the prior form 3 and prior form 7 have a weight gain of nearly 20% at 80% RH, which indicates that the hygroscopicity of form III is remarkably lower than prior crystalline forms. Low hygroscopicity can prevent the drug from deteriorating or deliquescent due to absorption of water during production and storage, which is of great significance for drug quality control. In addition, the interchange of prior form 3 and prior form 7 will happen at different relative humidity, which is particularly unfavorable for production. On the contrary, form III remains stable throughout the whole DVS procedure. Therefore, form III is more suitable for drug development.

EXAMPLE 10 CONVERSION RELATIONSHIP BETWEEN FORM III AND PRIOR FORM 7

Prior form 7 as starting material was stirred at room temperature in solvent systems with different water activities for 6 days, and tested. The XRPD results showed that prior form 7 converted to form III in all experiments, and the result is shown in table 9.

TABLE 9

Slurry of prior form 7 in different water activities

| Solvent (volume ratio) | Water activity | Initial crystalline form | Final crystalline form |
|---|---|---|---|
| H₂O/IPA = 1:99 | 0.12 | Prior form 7 | Form III of the present disclosure |
| H₂O/IPA = 3:97 | 0.3 | Prior form 7 | Form III of the present disclosure |
| H₂O/IPA = 6:94 | 0.5 | Prior form 7 | Form III of the present disclosure |
| H₂O/IPA = 11:89 | 0.7 | Prior form 7 | Form III of the present disclosure |
| H₂O/IPA = 23:77 | 0.9 | Prior form 7 | Form III of the present disclosure |

The result of this experiment indicates that prior form 7 will convert to form III in the presence of water. Whether in the API production or in the formulation production or in the drug storage procedure, the participation of water in the environment or the preparation condition cannot be avoided, so that crystalline transition in the presence of water can be a great hidden trouble to the quality control of the drug. Therefore, it is necessary to develop a crystalline form which is stable in the presence of water, and form III of the present disclosure can be stable in the presence of water, which has higher application value.

EXAMPLE 11 STABILITY OF FORM II

Figure 22:
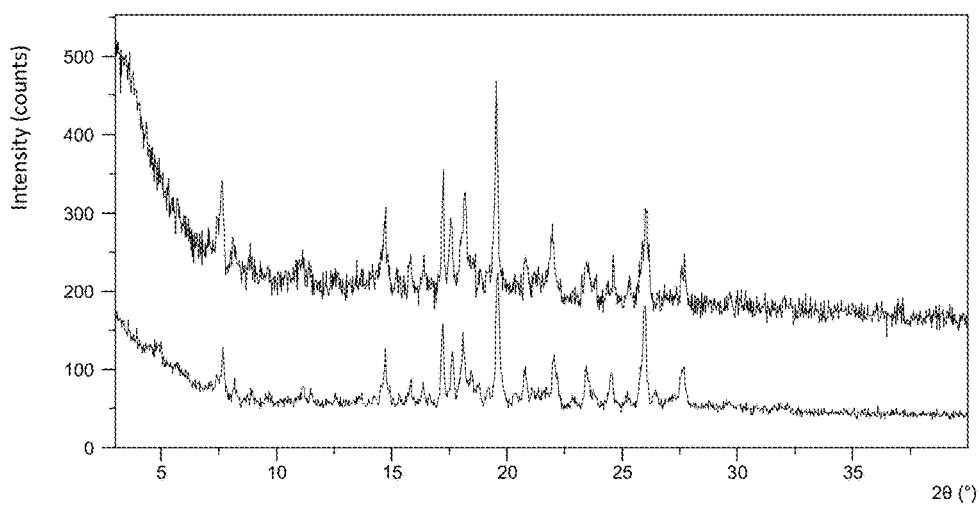
FIG. 22 shows an XRPD overlay pattern of form II before and after stored for 90 days. The above pattern is before stored and the below pattern is after stored.

Form II obtained from example 3 was stored under 25° C./60% RH for 90 days. XRPD patterns were collected before and after stored for 15 days, 30 days and 90 days. The result summarized in table 10 shows that form II has good stability, The XRPD patterns of form II before and after stored for 90 days are shown in FIG. 22.

TABLE 10

Stability of Form II

25° C./60%RH

| Test time | Purity % | Crystalline form after storage |
|---|---|---|
| Initial | 99.64 | Form II |
| 15 days | 99.50 | Form II |
| 30 days | 99.78 | Form II |
| 90 days | 99.52 | Form II |

Figure 23:
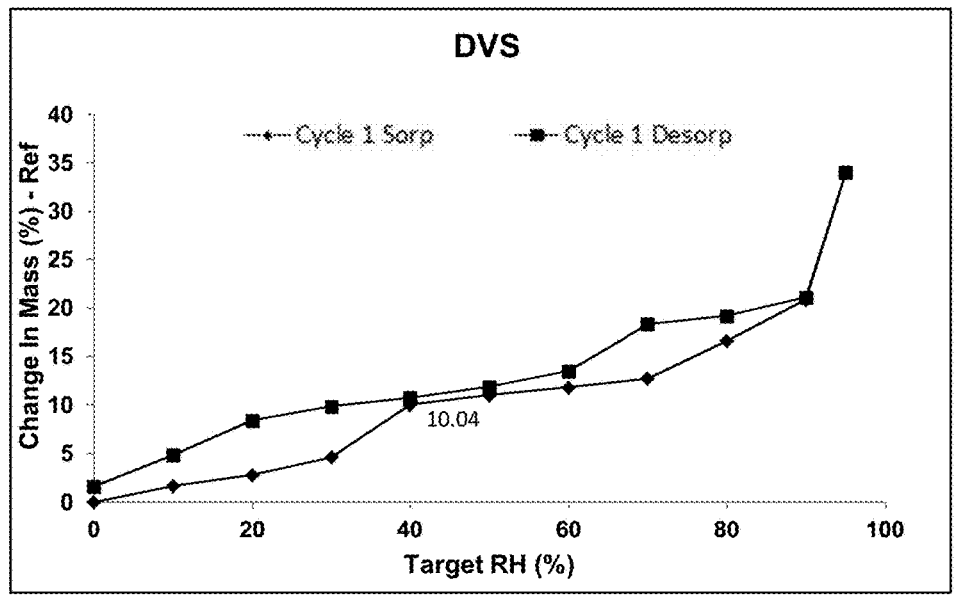
FIG. 23-25 shows DVS plots of prior form 7, form I and form II of the present disclosure respectively. The three forms were subjected to 0-95%-0 relative humidity cycle at 25° C.

EXAMPLE 12 HYGROSCOPICITY OF FORM I AND FORM II 6.5 mg of prior form 7 was placed in a DVS instrument, and subjected to a cycle of 0-95%-0RH at 25° C., the DVS plot is shown in FIG. 23.

Figure 24:
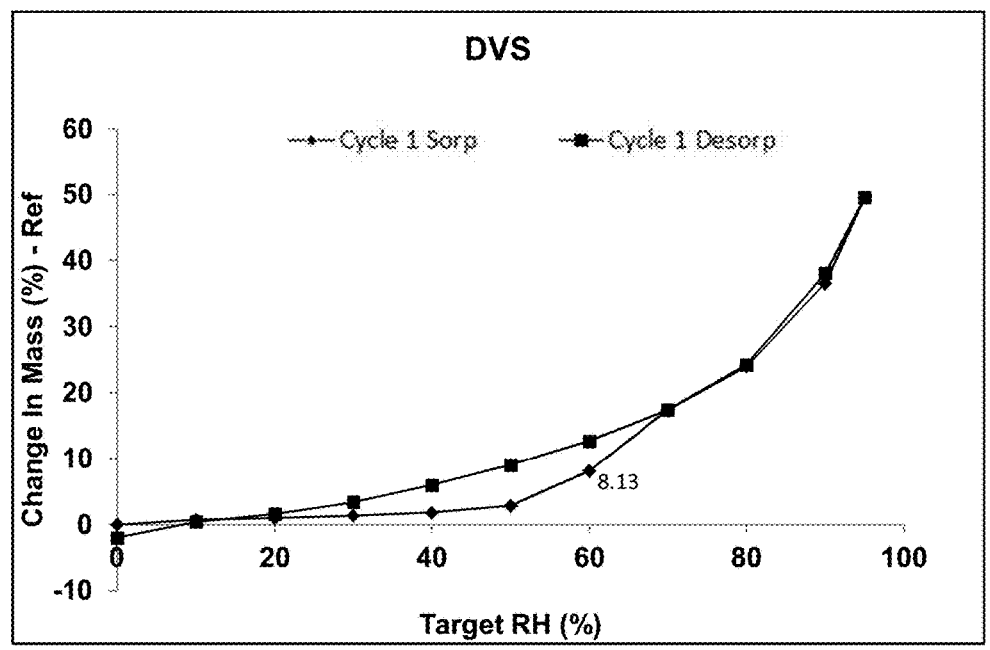

9.2 mg of Form I was placed in a DVS instrument, and subjected to a cycle of 0-95%-0RH at 25° C., the DVS plot is shown in FIG. 24.

Figure 25:
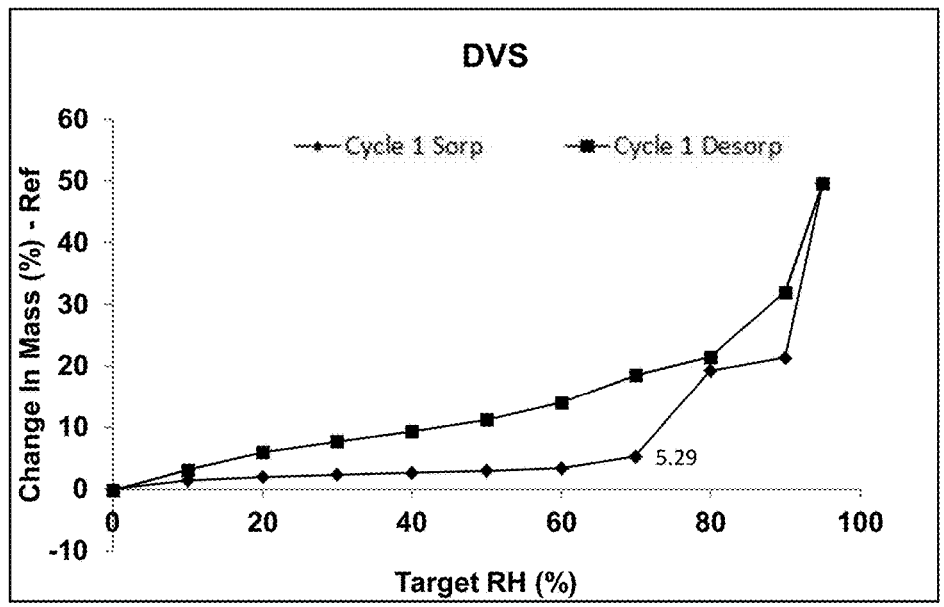
Figure 26:
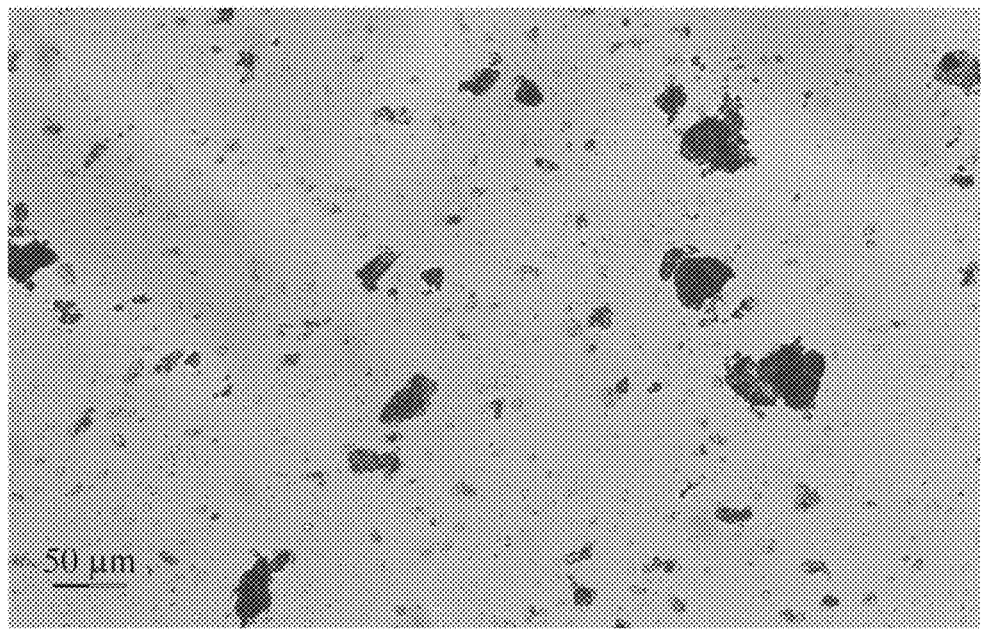
FIG. 26-29 shows the PLM images of form I, form II of the present disclosure, and prior form 3, prior form 7 respectively.
Figure 27:
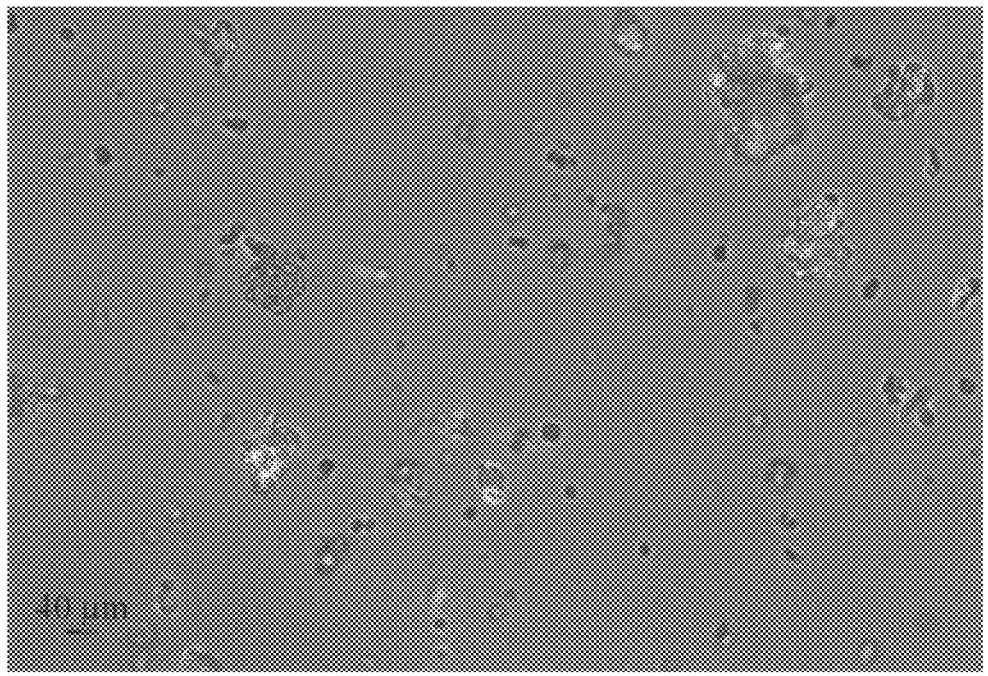
Figure 28:
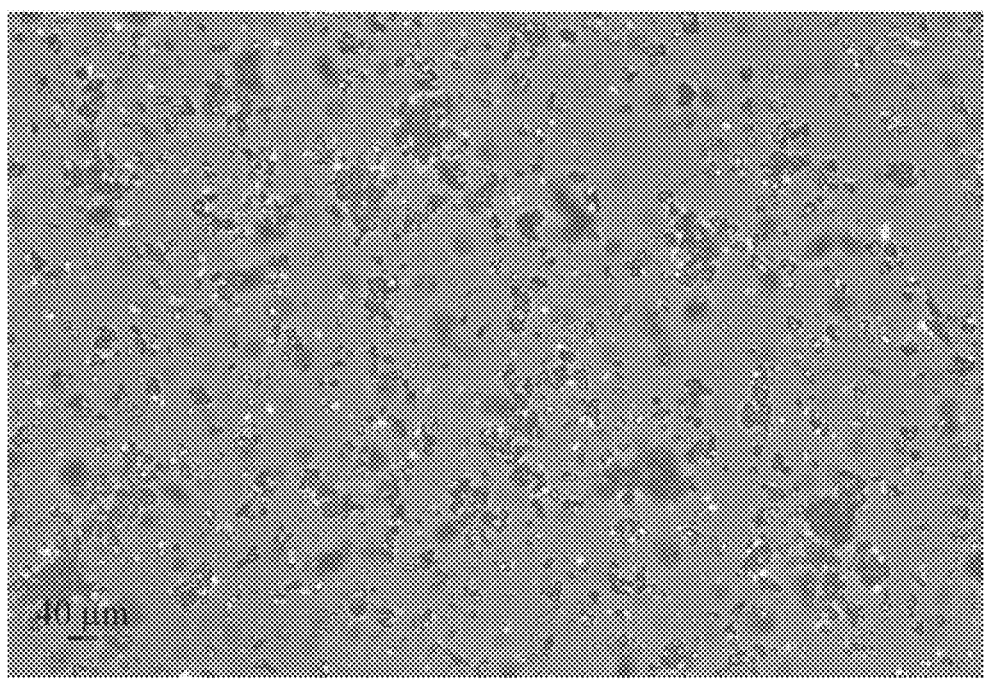
Figure 29:
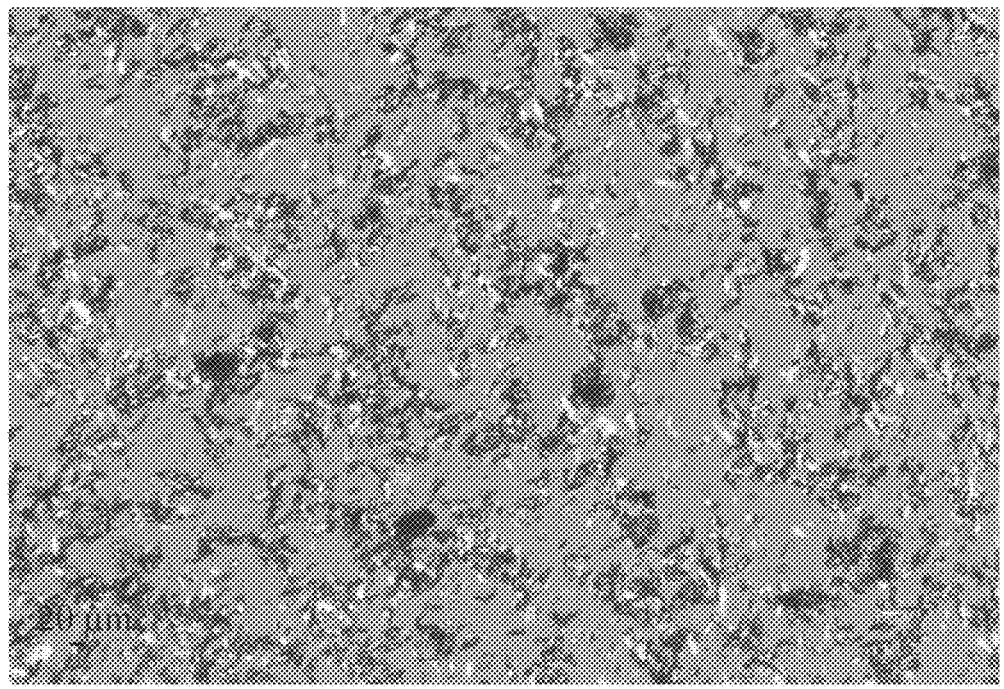

3.6 mg of Form II was placed in a DVS instrument and subjected to a cycle of 0-95%-0RH at 25° C., the DVS plot is shown in FIG. 25.

Hygroscopic data of prior form 7, form I and form II are shown in Table 11. As shown in FIG. 23 and Table 11, prior form 7 is hygroscopic, with a weight gain of 10% at 40% RH. Form I and form II show obvious advantages in hygroscopicity at 0~60% RH. Form II is stable at 0-70% RH and doesn't show obvious weight gain.

TABLE 11

Hygroscopicity data

| Crystalline form | Weight gain | | | | | |
|---|---|---|---|---|---|---|
| | 10% RH/% | 20% RH/% | 30% RH/% | 40% RH/% | 50% RH/% | 60% RH/% |
| Prior form 7 | 1.68 | 2.78 | 4.61 | 10.04 | 11.00 | 11.83 |
| Form I of the present disclosure | 0.69 | 0.99 | 1.33 | 1.82 | 2.82 | 8.13 |
| Form II of the present disclosure | 1.41 | 1.98 | 2.34 | 2.65 | 2.95 | 3.35 |

EXAMPLE 13 MORPHOLOGY AND PARTICLE SIZE STUDY

PLM and PSD of form I, form II of the present disclosure and prior form 3, prior form 7 were tested. The PLM images are shown in FIGS. 26, 27, 28, and 29, and the PSD data are shown in Table 12.

TABLE 12

PSD data

| | D(10)/μm | D(50)/μm | D(90)/μm |
|---|---|---|---|
| Prior form 3 | 1.67 | 12.79 | 76.41 |
| Prior form 7 | 3.41 | 9.37 | 37.69 |
| Form I of the present disclosure | 10.23 | 62.54 | 240.0 |
| Form II of the present disclosure | 4.15 | 27.48 | 128.7 |

It can be seen from the PLM and PSD data that the particle size of form I and form II of the present disclosure is larger than that of prior form 3 and prior form 7, and the size is suitable for product separation in the preparation process.

EXAMPLE 14 SOLUBILITY COMPARISON OF FORM I, FORM II OF THE PRESENT DISCLOSURE AND PRIOR FORM 3

Saturated solutions of form I, form II of the present disclosure and prior form 3 in both acetone and tetrahydrofuran (THF) were prepared, and concentrations in the saturation solutions were measured after 24 hours by high performance liquid chromatography (HPLC), and the results are shown in Table 13.

TABLE 13

Solubility of form I, form II of the present disclosure and prior form 3

| | Solubility | | |
|---|---|---|---|
| Solvent | Form I(mg/mL) | Form II (mg/mL) | Prior form 3 (mg/mL) |
| Acetone | 0.061 | 0.026 | 0.012 |
| Tetrahydrofuran | 0.048 | 0.018 | 0.013 |

It can be seen from the above comparison results that the solubility in acetone and THF after being stored for 24 hours of form I, form II of the present disclosure is about 1.5 to 5 times higher than that of prior form 3. Higher solubility can promote effective dissolution of API in the preparation process, and reduce the amount of the solvent, decrease energy consumption and release environmental pressure, which has significant application value.

EXAMPLE 15 STABILITY OF FORM III

Figure 30:
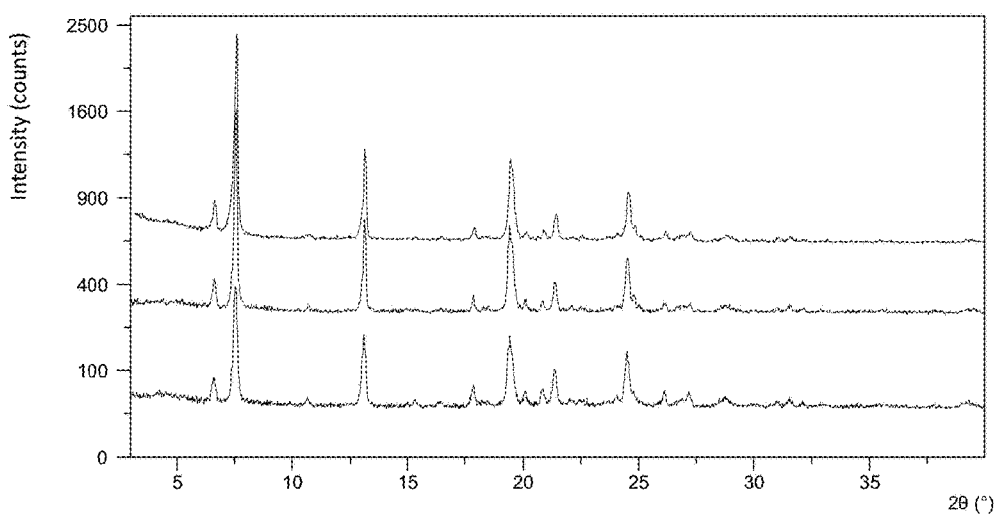
FIG. 30 shows an XRPD overlay pattern of form III before and after stored for 300 days (the above pattern is before stored, the middle pattern is after stored at 25° C./60% RH for 300 days and the below pattern is after stored at 40° C./75% RH for 300 days).

Form III was stored under 25° C./60% RH and 40° C./75% RH for 300 days. XRPD patterns were collected after stored for 15 days, 30 days and 300 days. The results summarized in table 14 show that form III has good stability. The XRPD pattern of form III is shown in FIG. 30.

TABLE 14

Stability of Form III

| | 25° C. /60%RH | | 40° C. /75%RH | |
| --- | --- | --- | --- | --- |
| Test time | Purity % | Crystalline form after storage | Purity % | Crystalline form after storage |
| initial | 99.82 | Form III | 99.82 | Form III |
| 15 days | 99.71 | Form III | 99.68 | Form III |
| 30 days | 99.78 | Form III | 99.73 | Form III |
| 300 days | 99.56 | Form III | 99.47 | Form III |

EXAMPLE 16 CONVERSION RELATIONSHIP BETWEEN FORM III AND PRIOR FORM 3

Prior form 3 was stirred at room temperature in solvent systems with different water activities for 4 days, then the solid was tested. The XRPD result was shown in table 15. The results show that prior form 3 is less stable than form III of the present disclosure in the presence of water.

TABLE 15

Stirring experiments of prior form 3 in different water activity systems

| Solvent (volume ratio) | Water activity | Initial crystalline form | Final crystalline form |
| --- | --- | --- | --- |
| H₂O/IPA = 1:99 | 0.12 | Prior form 3 | Form III of the present disclosure + a little prior form 3 |
| H₂O/IPA = 23:77 | 0.90 | Prior form 3 | Form III of the present disclosure |

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A crystalline form I of compound (I) dimesylate, wherein the X-ray powder diffraction pattern shows characteristic peaks at 2theta values of 5.9°±0.2°, 13.5°±0.2° and 21.8°±0.2°

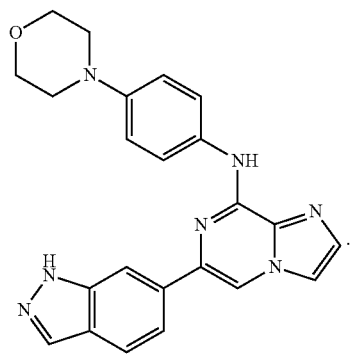

(I)

2. The crystalline form I according to claim 1, wherein the X-ray powder diffraction pattern further shows one or two or three characteristic peaks at 2theta values of 25.9°±0.2°, 17.1°±0.2° and 20.4°±0.2°.

3. The crystalline form I according to claim 1, wherein the X-ray powder diffraction pattern further shows one or two or three characteristic peaks at 2theta values of 10.6°±0.2°, 14.7°±0.2° and 17.7°±0.2°.

4. The crystalline form I according to claim 1, wherein said crystalline form I is a hydrate.

5. A preparation method of crystalline form I according to claim 1, wherein the method comprises: a) adding compound (I) dimesylate into a mixed system of alcohol solvents and aromatic hydrocarbon solvents and stirring at 5-30° C.; b) filtering the suspension of step a) and drying the filter cake to obtain crystalline form I.

6. The preparation method of crystalline form I according to claim 5, wherein the volume ratio of said alcohol solvents to aromatic hydrocarbon solvents varies from 1:1 to 1:5.

7. The preparation method of crystalline form I according to claim 5, wherein said alcohol solvent is methanol, and aromatic hydrocarbon solvent is p-xylene.

8. A crystalline form II of compound (I) dimesylate, wherein the X-ray powder diffraction pattern shows characteristic peaks at 2theta values of 15.8°±0.2°, 17.2°±0.2° and 19.5°±0.2°

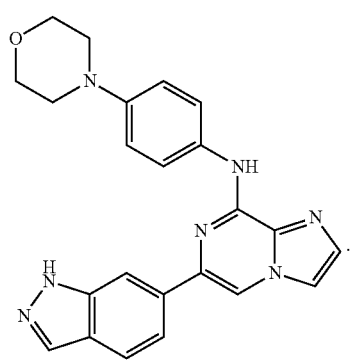

(I)

9. The crystalline form II according to claim 8, wherein the X-ray powder diffraction pattern further shows one or two or three characteristic peaks at 2theta values of 26.1°±0.2°, 14.7°±0.2° and 21.9°±0.2°.

10. The crystalline form II according to claim 8, wherein the X-ray powder diffraction pattern further shows one or two or three characteristic peaks at 2theta values of 7.6°±0.2°, 18.2°±0.2° and 27.8°±0.2°.

11. The crystalline form II according to claim 8, wherein said crystalline form II is a hydrate.

12. A preparation method of crystalline form II according to claim 8, wherein the method comprises: a) adding compound (I) dimesylate into one or more aromatic hydrocarbon solvents, and stirring at 40-80° C.; b) filtering the suspension of step a) and drying the filter cake to obtain crystalline form II.

13. The preparation method according to claim 12, wherein said aromatic hydrocarbon solvent is toluene or p-xylene.

14. The preparation method according to claim 12, wherein said stirring is at 60-70° C.

15. A crystalline form III of compound (I) monomesylate, wherein the X-ray powder diffraction pattern shows characteristic peaks at 2theta values of 7.4°±0.2°, 12.9°±0.2° and 19.2°±0.2°

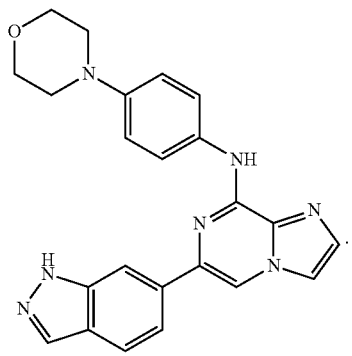

(I)

16. The crystalline form III according to claim 15, wherein the X-ray powder diffraction pattern further shows one or two or three characteristic peaks at 2theta values of 6.5°±0.2°, 21.2°±0.2° and 24.4°±0.2°.

17. The crystalline form III according to claim 15, wherein the X-ray powder diffraction pattern further shows one or two or three characteristic peaks at 2theta values of 17.7°±0.2°, 20.7°±0.2° and 26.0°±0.2°.

18. The crystalline form III according to claim 15, wherein said crystalline form III is an anhydrate.

19. A preparation method of crystalline form III according to claim 15, wherein said method comprises either step a) and c) or step b) and c):
a) Adding compound (I) into a mixed solvent of ketones and water, adding methanesulfonic acid while stirring, continuing stirring;
b) Adding compound (I) dimesylate into a mixed solvent of alcohols and water, and stirring;
c) Filtering the suspension of step a) or b) and drying the filter cake to obtain crystalline form III.

20. The preparation method of crystalline form III according to claim 19, wherein, in step a), the volume ratio of said ketones to water varies from 1:1 to 10:1.

21. The preparation method of crystalline form III according to claim 19, wherein said ketone is acetone.

22. The preparation method of crystalline form III according to claim 19, wherein, in step a), the molar ratio of said methanesulfonic acid to compound (I) vary from 1.0:1 to 1.8:1.

23. The preparation method of crystalline form III according to claim 19, wherein, in step a), said stirring is at 5-50° C.

24. The preparation method of crystalline form III according to claim 19, wherein, in step b), the volume ratio of said alcohol solvents and water varies from 99:1 to 1:99.

25. The preparation method of crystalline form III according to claim 19, wherein said alcohol is isopropanol.

26. The preparation method of crystalline form III according to claim 19, wherein, in step b), said stirring is at 25-60° C.

27. A pharmaceutical composition, comprising a therapeutically effective amount of crystalline form I according to claim 1, and at least one pharmaceutically acceptable carrier or excipient.

28. A pharmaceutical composition, comprising a therapeutically effective amount of crystalline form II according to claim 8, and at least one pharmaceutically acceptable carrier or excipient.

29. A pharmaceutical composition, comprising a therapeutically effective amount of crystalline form III according to claim 15, and at least one pharmaceutically acceptable carrier or excipient.

* * * * *